US008691231B2

(12) United States Patent
Bukhalid et al.

(10) Patent No.: US 8,691,231 B2
(45) Date of Patent: Apr. 8, 2014

(54) METHODS OF TREATMENT OF TUMORS EXPRESSING PREDOMINANTLY HIGH AFFINITY EGFR LIGANDS OR TUMORS EXPRESSING PREDOMINANTLY LOW AFFINITY EGFR LIGANDS WITH MONOCLONAL AND OLIGOCLONAL ANTI-EGFR ANTIBODIES

(75) Inventors: Raghida Bukhalid, Melrose, MA (US); Ulrik Nielsen, Quincy, MA (US); Shannon Werner, Belmont, MA (US); Jeffrey David Kearns, Arlington, MA (US)

(73) Assignee: Merrimack Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/488,270

(22) Filed: Jun. 4, 2012

(65) Prior Publication Data
US 2012/0308576 A1 Dec. 6, 2012

Related U.S. Application Data

(60) Provisional application No. 61/493,252, filed on Jun. 3, 2011, provisional application No. 61/504,633, filed on Jul. 5, 2011, provisional application No. 61/558,945, filed on Nov. 11, 2011.

(51) Int. Cl.
*A61K 39/395* (2006.01)
*G01N 33/567* (2006.01)
*A61K 38/18* (2006.01)
*A61P 35/00* (2006.01)

(52) U.S. Cl.
USPC ......... 424/141.1; 436/503; 514/7.6; 514/19.3

(58) Field of Classification Search
None
See application file for complete search history.

(56) References Cited

U.S. PATENT DOCUMENTS

| 7,226,592 B2 | 6/2007 | Kreysch |
| 7,498,142 B2 | 3/2009 | Yarden et al. |
| 7,771,958 B2 * | 8/2010 | Bacus et al. ............... 435/7.23 |
| 7,887,805 B2 * | 2/2011 | Pedersen et al. ........... 424/143.1 |
| 2004/0052785 A1 | 3/2004 | Goodman et al. |
| 2005/0003403 A1 | 1/2005 | Rossi et al. |
| 2006/0228355 A1 | 10/2006 | Laeremans et al. |
| 2008/0206236 A1 | 8/2008 | Haurum |
| 2008/0299120 A1 | 12/2008 | Miller et al. |
| 2009/0004192 A1 | 1/2009 | Pedersen et al. |
| 2009/0155288 A1 | 6/2009 | Yarden et al. |
| 2011/0287002 A1 | 11/2011 | Bukhalid et al. |

FOREIGN PATENT DOCUMENTS

| WO | 02/055106 A2 | 7/2002 |
| WO | 2004/032961 A1 | 4/2004 |
| WO | 2004/094613 A2 | 11/2004 |
| WO | 2008/095504 A1 | 8/2008 |
| WO | 2008/104183 A2 | 9/2008 |
| WO | 2010/019952 A2 | 2/2010 |
| WO | 2011/140151 A1 | 11/2011 |
| WO | 2011/140254 A1 | 11/2011 |

OTHER PUBLICATIONS

Baker, J.B. et al., "Tumour gene expression predicts response to cetuximab in patients with KRAS wild-type metastatic colorectal cancer," British Journal of Cancer, vol. 104:488-495 (2011).
Grandis, Jennifer Rubin et al., "Levels of TGF-alpha and EGFR Protein in Head and Neck Squamous Cell Carcinoma and Patient Survival," Journal of the National Cancer Institute, vol. 90(11):824-832 (1998).
Hatakeyama, Hiromitsu et al., "Regulation of Heparin-Binding EGF-Like Growth Factor by MiR-212 and Acquired Cetuximab-Resistance in Head and Neck Squamous Cell Carcinoma," PLoS One, vol. 5(9):e12702, 1-13 (2010).
Saridaki, Zacharenia et al., "Impact of KRAS, BRAF, PIK3CA Mutations, PTEN, AREG, EREG Expression and Skin Rash in 2nd Line Cetuximab-Based Therapy of Colotectal Cancer Patients," PLoS One, vol. 6(1):e15980, 1-13 (2011).
Schoeberl, Birgit et al., "Therapeutically Targeting ErbB3: A Key Node in Ligand-Induced Activation of the ErbB Receptor-PI3K Axis," Science Signaling, vol. 2(77):ra31, 1-14 (2009).
Siena, Salvatore et al., "Biomarkers Predicting Clinical Outcome of Epidermal Growth Factor Receptor-Targeted Therapy in Metastatic Colorectal Cancer," J. Natl. Cancer, vol. 101:1-17 (2009).
Tabernero, Josep et al., "Pharmacogenomic and Pharmacoproteomic Studies of Cetuximab in Metastatic Colorectal Cancer: Biomarker Analysis of a Phase I Dose-Escalation Study," J. Clin. Oncol., vol. 28:1181-1189 (2010).
Yonesaka, Kimio et al., "Autocrine Production of Amphiregulin Predicts Sensitivity to Both Gefitinib and Cetuximab and EGFR Wild-type Cancers," Clin. Cancer Res., vol. 14(21):6963-6973 (2008).
European Search Report for European Application No. 12275088.8, 12 pages, dated Oct. 11, 2012.
ClinicalTrials.gov, "A Phase I Study of Cetuximab in Combination With Gefitinib in Patients With Advanced/Metastatic Non-Small Cell Lung Cancer," Study NCT00162318, Bristol-Myers Squibb, 3 pages.
ClinicalTrials.gov, "A Study of BIBW 2992 (Afatinib) in Patients With Metastatic Colorectal Cancer," Study NCT01152437, Boehringer Ingelheim Pharmaceuticals, 4 pages.
ClinicalTrials.gov, "A Study of R1507 in Combination With Multiple Standard Chemotherapy Treatments in Patients With Advanced Solid Tumors," Study NCT00811993, Hoffmann-La Roche, 6 pages.

(Continued)

*Primary Examiner* — Elly-Gerald Stoica
(74) *Attorney, Agent, or Firm* — Nelson Mullins Riley & Scarborough LLP; Jane E. Remillard, Esq.; Jill Gorny Sloper, Esq.

(57) ABSTRACT

Disclosed are pharmaceutical preparations for, and methods for determining, appropriate and effective treatment with therapeutic agents comprising a single species of anti-EGFR monoclonal antibody or therapeutic agents comprising a plurality of species of such antibodies, as well as kits useful for making such determinations.

17 Claims, 22 Drawing Sheets

(56) References Cited

OTHER PUBLICATIONS

ClinicalTrials.gov, "A Study of SCH 717454 in Combination With Different Treatment Regimens in Subjects With Advanced Solid Tumors (P04722)," Study NCT00954512, Schering-Plough, 5 pages.
ClinicalTrials.gov, "An Umbrella, Modular Study Based on Epidermal Growth Factor Receptors (EGFR) Mutation Status," Study NCT00903734, M.D. Anderson Cancer Center, 5 pages.
ClinicalTrials.gov, "Bevacizumab in Multiple Phase I Combinations," Study NCT00543504, M.D. Anderson Cancer Center, 7 pages.
ClinicalTrials.gov, "Bevacizumab and Gemcitabine Combined With Either Cetuximab or Erlotinib in Treating Patients With Advanced Pancreatic Cancer," Study NCT00091026, National Cancer Institute (NCI), 6 pages.
ClinicalTrials.gov, "BIBW 2992 (Afatinib) in Head & Neck Cancer," Study NCT00514943, Boehringer Ingelheim Pharmaceuticals, 5 pages.
ClinicalTrials.gov, "Carboplatin, Paclitaxel, Cetuximab, and Erlotinib Hydrochloride in Treating Patients With Metastatic or Recurrent Head and Neck Squamous Cell Cancer," Study NCT01316757, Fox Chase Cancer Center, 7 pages.
ClinicalTrials.gov, "Cetuximab in Patients With Lung Adenocarcinoma Receiving Erlotinib That Have Developed 'Acquired Resistance' to Erlotinib," Study NCT00716456, Memorial Sloan-Kettering Cancer Center, 1 page.
ClinicalTrials.gov, "Clinical and Pathologic Studies of Patients Undergoing Treatment With EGFR Inhibitors," Study NCT01137162, Stanford University, 1 page.
ClinicalTrials.gov, "Combination Study of BMS-754807 and Erbitux in Subjects With Advanced or Metastatic Solid Tumors," Study NCT00908024, Bristol-Myers Squibb, 4 pages.
ClinicalTrials.gov, "Dual Epidermal Growth Factor Receptor Inhibition With Erlotinib and Panitumumab With or Without Chemotherapy for Advanced Colorectal Cancer," Study NCT00940316, Northwestern University, 1 page.
ClinicalTrials.gov, "Dual Inhibition of EGFR Signalling Using the Combination of Cetuximab and Erlotinib (Dux)," Study NCT00784667, Austin Health, 1 page.
ClinicalTrials.gov, "Erlotinib and Cetuximab With or Without Bevacizumab in Treating Patients With Metastatic or Unresectable Kidney, Colorectal, Head and Neck, Pancreatic, or Non-Small Cell Lung Cancer," Study NCT00101348, National Cancer Institute (NCI), 6 pages.
ClinicalTrials.gov, "Erlotinib and Cetuximab in Treating Patients With Advanced Gastrointestinal Cancer, Head and Neck Cancer, Non-Small Cell Lung Cancer, or Colorectal Cancer," Study NCT00397384, Vanderbilt-Ingram Cancer Center, 1 page.
ClinicalTrials.gov, "Erlotinib and Cetuximab in Treating Patients With Advanced Solid Tumors With Emphasis on Non-Small Cell Lung Cancer," Study NCT00408499, University of California, Davis, 1 page.
ClinicalTrials.gov, "Erlotinib and Gemcitabine With or Without Panitumumab in Treating Patients With Metastatic Pancreatic Cancer," Study NCT00550836, National Cancer Institute (NCI), 6 pages.
ClinicalTrials.gov, "Erlotinib in Combination With Cetuximab," Study NCT00895362, M.D. Anderson Cancer Center, 5 pages.
ClinicalTrials.gov, "Evaluating Preventive Therapy With Oint Threolone, Synthomycine or Aqua Cream Lotion, for EGFR'I Induced Acneiform Rash," Study NCT01256437, Rabin Medical Center, 4 pages.
ClinicalTrials.gov, "Histological Characterization and Differentiation of Rash From Other Epidermal Growth Factor Receptor (EGFR) Inhibitors," Study NCT00709878, Northwestern University, 1 page.
ClinicalTrials.gov, "Individualized Drug Treatment Selection Process for Treating Patients with Pancreatic Cancer That Can Be Removed by Surgery," Study NCT00276744, Sidney Kimmel Comprehensive Cancer Center, 5 pages.
ClinicalTrials.gov, "Lapatinib and Cetuximab in Patients With Solid Tumors (TYKERB-ITUX 1)," Study NCT01184482, Georgetown University, 4 pages.
ClinicalTrials.gov, "Menadione Topical Lotion in Treating Skin Discomfort and Psychological Distress in Patients With Cancer Receiving Panitumumab, Erlotinib Hydrochloride, or Cetuximab," Study NCT01393821, Mayo Clinic, 5 pages.
ClinicalTrials.gov, "Pharmocokinetic/Pharmacodynamic (PK/PD) Study of the Combination Cetuximab/Gefitinib," Study NCT00820417, Harrison Clinical Research, 1 page.
ClinicalTrials.gov, "Pharmacodynamic Separation of Pemetrexed and Erlotinib as Second-line Therapy in Patients With Advanced Non-small Cell Lung Cancer (NSCLC)," Study NCT00950365, Montefiore Medical Center, 1 page.
ClinicalTrials.gov, "Phase 1 Trial With SIR-Spheres and Cetuximab +/- Erlotinib," Study NCT01432119, M.D. Anderson Cancer Center, 6 pages.
ClinicalTrials.gov, "Safety and Efficacy of Radiation/Cetuximab Plus EGFR Antisense DNA for Head and Neck Squamous Cell Carcinoma," Study NCT00903461, University of Pittsburgh, 5 pages.
ClinicalTrials.gov, "Study About Preventive Treatment of Folliculitis Induced by Epidermal Growth Factor Receptor (EGF-R) Inhibitors (DIPROCOL)," Study NCT00910676, Centre Oscar Lambret, 4 pages.
ClinicalTrials.gov, "Study of AMG 479 With Biologics or Chemotherapy for Subjects With Advanced Solid Tumors," Study NCT00974896, Amgen, 5 pages.
ClinicalTrials.gov, "Study of Cetuximab in Combination With Tarceva in Patients With Solid Tumors," Study NCT00207077, Bristol-Myers Squibb, 3 pages.
ClinicalTrials.gov, "Sym004 in Patients With Advanced Solid Tumors," Study NCT01117428, Symphogen A/S, 1 page.
ClinicalTrials.gov, "Sym004 in SCCHN Patients Failing Anti-EGFR Based Therapy," Study NCT01417936, Symphogen A/S, 1 page.
ClinicalTrials.gov, "Temsirolimus (Torisel) and Erlotinib (Tarceva) in Platinum-Refractory/Ineligible, Advanced, Squamous Cell Carcinoma," Study NCT01009203, New Mexico Cancer Care Alliance, 4 pages.
ClinicalTrials.gov, "Tetracycline in Preventing Skin Rash in Patients Who Are Receiving Drugs Such as Gefitinib and Cetuximab for Cancer," Study NCT00091247, National Cancer Institute (NCI), 1 page.
ClinicalTrials.gov, "Topical Sunscreen in Preventing Skin Rash in Patients Receiving Drugs Such as Erlotinib or Cetuximab for Cancer," Study NCT00362986, National Cancer Institute (NCI), 4 pages.
ClinicalTrials.gov, "Trial of BIBW 2992 (Afatinib) + Cetuximab in Non-Small Cell Lung Cancer," Study NCT01090011, Boehringer Ingelheim Pharmaceuticals, 1 page.
ClinicalTrials.gov, "Validation of Cancer Questionnaire for Skin Toxicities in Patients With Colorectal Cancer or Lung Cancer Receiving Cetuximab, Panitumumab, or Erlotinib Hydrochloride," Study NCT01416688, National Cancer Institute (NCI), 5 pages.
ClinicalTrials.gov, "ZD6474, Cetuximab, and Irinotecan in Patients With Metastatic Colorectal Cancer," Study NCT00436072, Dana-Farber Cancer Institute, 5 pages.
Fogler, William E. et al., "Enhanced Cytotoxicity against Colon Carcinoma by Combinations of Noncompeting Monoclonal Antibodies to the 17-1A Antigen," Cancer Research, vol. 48:6303-6308 (1998).
Friedman, Lilach M. et al., "Synergistic down-regulation of receptor tyrosine kinases by combinations of mAbs: Implications for cancer innumotherapy," PNAS, vol. 102(6):1915-1920 (2005).
Kamat, Vishal et al., "Enhanced EGFR inhibition and distinct epitope recognition by EGFR antagonistic mAbs C225 and 425," Cancer Biology & Therapy, vol. 7(5):726-733 (2008).
Nahta, Rita et al., "The HER-2-Targeting Antibodies Trastuzumab and Pertuzumab Synergistically Inhibit the Survival of Breast Cancer Cells," Cancer Research, vol. 64:2343-2346 (2004).
Nowakowski, A. et al., "Potent neutralization of botulinum neurotoxin by recombinant oligoclonal antibody," PNAS, vol. 99(17):11346-11350 (2002).
Pedersen, Mikkel Wandahl et al., "Sym004: A Novel Synergistic Anti-Epidermal Growth Factor Receptor Antibody Mixture with Superior Anticancer Efficacy," Cancer Research, vol. 70(2):588-597 (2010).

(56) References Cited

OTHER PUBLICATIONS

Perera, Rushika M. et al., "Treatment of Human Tumor Xenografts with Monoclonal Antibody 806 in Combination with a Prototypical Epidermal Growth Factor Receptor-Specific Antibody Generates Enhanced Antitumor Activity," Clinical Cancer Research, vol. 11(17):6390-6399 (2005).

Regales, Lucia et al., "Dual targeting of EGFR can overcome a major drug resistance mutation in mouse models of EGFR mutant lung cancer," The Journal of Clinical Investigation, vol. 119(10):3000-3010 (2009).

Skartved, Niels Jorgen Ostergaard et al., "Preclinical Pharmacokinetics and Safety of Sym004: A Synergistic Antibody Mixture Directed against Epidermal Growth Factor Receptor," Clinical Cancer Research, vol. 17 (18):5962-5972 (2011).

Spangler, Jamie B. et al., "Combination antibody treatment down-regulates epidermal growth factor receptor by inhibiting endosomal recycling," PNAS, vol. 107(30):13252-13257 (2010).

Spiridon, Camelia I. et al., "Targeting Multiple Her-2 Epitopes with Monoclonal Antibodies Results in Improved Antigrowth Activity of a Human Breast Cancer Cell Line in Vitro and In Vivo," Clinical Cancer Research, vol. 8:1720-1730 (2002).

\* cited by examiner

SEQUENCE LISTING

```
<160> NUMBER OF SEQ ID NOS: 10

<210> SEQ ID NO 1
<211> LENGTH: 140
<212> TYPE: PRT
<213> ORGANISM: Homo sapiens

<400> SEQUENCE: 1

Met Gly Phe Gly Leu Ser Trp Leu Phe Leu Val Ala Ile Leu Lys Gly
1               5                   10                  15

Val Gln Cys Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ser Ser Tyr Ala Ile Ser Trp Val Arg Gln Ala Pro Gly Gln Gly Leu
    50                  55                  60

Glu Trp Met Gly Ser Ile Ile Pro Ile Phe Gly Thr Val Asn Tyr Ala
65                  70                  75                  80

Gln Lys Phe Gln Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Asp Pro Ser Val Asn Leu Tyr Trp Tyr Phe Asp
        115                 120                 125

Leu Trp Gly Arg Gly Thr Leu Val Thr Val Ser Ser
    130                 135                 140

<210> SEQ ID NO 2
<211> LENGTH: 127
<212> TYPE: PRT
<213> ORGANISM: Homo sapiens

<400> SEQUENCE: 2

Met Gly Thr Pro Ala Gln Leu Leu Phe Leu Leu Leu Leu Trp Leu Pro
```

-continued

```
               1               5                  10                 15
Asp Thr Thr Gly Asp Ile Gln Met Thr Gln Ser Pro Ser Thr Leu Ser
                        20                 25                 30

Ala Ser Val Gly Asp Arg Val Thr Ile Thr Cys Arg Ala Ser Gln Ser
                        35                 40                 45

Ile Ser Ser Trp Trp Ala Trp Tyr Gln Gln Lys Pro Gly Lys Ala Pro
             50                 55                 60

Lys Leu Leu Ile Tyr Asp Ala Ser Ser Leu Glu Ser Gly Val Pro Ser
 65                 70                 75                 80

Arg Phe Ser Gly Ser Gly Ser Gly Thr Glu Phe Thr Leu Thr Ile Ser
                        85                 90                 95

Ser Leu Gln Pro Asp Asp Phe Ala Thr Tyr Tyr Cys Gln Gln Tyr His
                       100                105                110

Ala His Pro Thr Thr Phe Gly Gly Gly Thr Lys Val Glu Ile Lys
                       115                120                125
```

<210> SEQ ID NO 3
<211> LENGTH: 138
<212> TYPE: PRT
<213> ORGANISM: Homo sapiens

<400> SEQUENCE: 3

```
Met Gly Phe Gly Leu Ser Trp Leu Phe Leu Val Ala Ile Leu Lys Gly
 1               5                  10                 15

Val Gln Cys Gln Val Gln Leu Val Gln Ser Gly Ala Glu Val Lys Lys
                        20                 25                 30

Pro Gly Ser Ser Val Lys Val Ser Cys Lys Ala Ser Gly Gly Thr Phe
                        35                 40                 45

Gly Ser Tyr Ala Ile Ser Trp Val Arg Gln Ala Pro Gly Gln Gly Leu
             50                 55                 60

Glu Trp Met Gly Ser Ile Ile Pro Ile Phe Gly Ala Ala Asn Pro Ala
 65                 70                 75                 80

Gln Lys Ser Gln Gly Arg Val Thr Ile Thr Ala Asp Glu Ser Thr Ser
                        85                 90                 95

Thr Ala Tyr Met Glu Leu Ser Ser Leu Arg Ser Glu Asp Thr Ala Val
                       100                105                110

Tyr Tyr Cys Ala Lys Met Gly Arg Gly Lys Val Ala Phe Asp Ile Trp
                       115                120                125

Gly Gln Gly Thr Met Val Thr Val Ser Ser
             130                135
```

<210> SEQ ID NO 4
<211> LENGTH: 133
<212> TYPE: PRT
<213> ORGANISM: Homo sapiens

<400> SEQUENCE: 4

```
Met Gly Thr Pro Ala Gln Leu Leu Phe Leu Leu Leu Trp Leu Pro
 1               5                  10                 15

Asp Thr Thr Gly Asp Ile Val Met Thr Gln Ser Pro Asp Ser Leu Ala
                        20                 25                 30

Val Ser Leu Gly Glu Arg Ala Thr Ile Asn Cys Lys Ser Ser Gln Ser
                        35                 40                 45

Val Leu Tyr Ser Pro Asn Asn Lys Asn Tyr Leu Ala Trp Tyr Gln Gln
             50                 55                 60

Lys Pro Gly Gln Pro Pro Lys Leu Leu Ile Tyr Trp Ala Ser Thr Arg
 65                 70                 75                 80
```

```
Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Gln Tyr Tyr Gly Ser Pro Ile Thr Phe Gly Gly Gly Thr
        115                 120                 125

Lys Val Glu Ile Lys
    130

<210> SEQ ID NO 5
<211> LENGTH: 142
<212> TYPE: PRT
<213> ORGANISM: Homo sapiens

<400> SEQUENCE: 5

Met Gly Phe Gly Leu Ser Trp Leu Phe Leu Val Ala Ile Leu Lys Gly
1               5                   10                  15

Val Gln Cys Gln Val Gln Leu Val Gln Ser Gly Ala Glu Val Lys Lys
            20                  25                  30

Pro Gly Ala Ser Val Lys Val Ser Cys Lys Ala Ser Gly Tyr Ala Phe
        35                  40                  45

Thr Ser Tyr Gly Ile Asn Trp Val Arg Gln Ala Pro Gly Gln Gly Leu
    50                  55                  60

Glu Trp Met Gly Trp Ile Ser Ala Tyr Asn Gly Asn Thr Tyr Tyr Ala
65                  70                  75                  80

Gln Lys Leu Arg Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Asp Leu Gly Gly Tyr Gly Ser Gly Ser Val Pro
        115                 120                 125

Phe Asp Pro Trp Gly Gln Gly Thr Leu Val Thr Val Ser Ser
    130                 135                 140

<210> SEQ ID NO 6
<211> LENGTH: 128
<212> TYPE: PRT
<213> ORGANISM: Homo sapiens

<400> SEQUENCE: 6

Met Gly Thr Pro Ala Gln Leu Leu Phe Leu Leu Leu Trp Leu Pro
1               5                   10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Val Ser Ser Asn Leu Ala Trp Tyr Gln Gln Lys Pro Gly Gln Ala Pro
    50                  55                  60

Arg Leu Leu Ile Tyr Gly Ala Ser Thr Arg Ala Thr Gly Ile Pro Ala
65                  70                  75                  80

Arg Phe Ser Gly Ser Gly Ser Gly Thr Glu Phe Thr Leu Thr Ile Ser
                85                  90                  95

Ser Leu Gln Ser Glu Asp Phe Ala Val Tyr Tyr Cys Gln Asp Tyr Arg
            100                 105                 110

Thr Trp Pro Arg Arg Val Phe Gly Gly Gly Thr Lys Val Glu Ile Lys
        115                 120                 125
```

<210> SEQ ID NO 7
<211> LENGTH: 125
<212> TYPE: PRT
<213> ORGANISM: Homo sapiens

<400> SEQUENCE: 7

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Tyr Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Thr Met Val Arg Gly Val Met Lys Asp Tyr Phe
            100                 105                 110

Asp Tyr Trp Gly Gln Gly Thr Leu Val Thr Val Ser Ser
        115                 120                 125

<210> SEQ ID NO 8
<211> LENGTH: 107
<212> TYPE: PRT
<213> ORGANISM: Homo sapiens

<400> SEQUENCE: 8

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
            20                  25                  30

Leu Val Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 9
<211> LENGTH: 123
<212> TYPE: PRT
<213> ORGANISM: Homo sapiens

<400> SEQUENCE: 9

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Tyr Ile Tyr Trp Val Lys Gln Arg Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

```
Lys Thr Lys Ala Thr Leu Thr Val Asp Glu Ser Ser Thr Thr Ala Tyr
 65                  70                  75                  80

Met Gln Leu Ser Ser Leu Thr Ser Glu Asp Ser Ala Val Tyr Tyr Cys
                 85                  90                  95

Thr Arg Gln Gly Leu Trp Phe Asp Ser Asp Gly Arg Gly Phe Asp Phe
            100                 105                 110

Trp Gly Gln Gly Thr Thr Leu Thr Val Ser Ser
        115                 120

<210> SEQ ID NO 10
<211> LENGTH: 112
<212> TYPE: PRT
<213> ORGANISM: Homo sapiens

<400> SEQUENCE: 10

Asp Val Leu Met Thr Gln Ile Pro Leu Ser Leu Pro Val Ser Leu Gly
 1               5                  10                  15

Asp Gln Ala Ser Ile Ser Cys Arg Ser Ser Gln Asn Ile Val His Ser
                20                  25                  30

Asn Gly Asn Thr Tyr Leu Asp Trp Tyr Leu Gln Lys Pro Gly Gln Ser
            35                  40                  45

Pro Asn Leu Leu Ile Tyr Lys Val Ser Asn Arg Glu Ser Gly Val Pro
        50                  55                  60

Asp Arg Phe Arg Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Tyr
                 85                  90                  95

Ser His Val Pro Trp Thr Phe Gly Gly Gly Thr Lys Leu Glu Ile Lys
            100                 105                 110
```

METHODS OF TREATMENT OF TUMORS EXPRESSING PREDOMINANTLY HIGH AFFINITY EGFR LIGANDS OR TUMORS EXPRESSING PREDOMINANTLY LOW AFFINITY EGFR LIGANDS WITH MONOCLONAL AND OLIGOCLONAL ANTI-EGFR ANTIBODIES

RELATED APPLICATIONS

This application claims the benefit of U.S. Provisional Application No. 61/493,252, filed on Jun. 3, 2011, U.S. Provisional Application No. 61/504,633, filed on Jul. 5, 2011, and U.S. Provisional Application No. 61/558,945, filed on Nov. 11, 2011, the entire contents of which are incorporated by reference herein.

BACKGROUND

The epidermal growth factor receptor (EGFR) is a cell surface transmembrane receptor of the HER/ErbB receptor family that transmits signals (including mitogenic signals that drive cell proliferation) to the interior of a cell when activated, typically by the binding of any of a number of extracellular ligands such as epidermal growth factor (EGF). EGFR ligands vary in their affinity for EGFR and are categorized as either high- or low-affinity ligands. It is thought that the high- and low-affinity interactions between EGFR and its ligands activate different signaling pathways. This signal transmission occurs through a cascade of intracellular events beginning with protein phosphorylation mediated by receptor tyrosine kinase activity. EGFR has proven a responsive target for anti-proliferative (e.g., anti-cancer) drugs, including "small molecule" tyrosine kinase inhibitor drugs (typically no larger than 700-900 AMU) that may be orally administered as well as monoclonal antibody based drugs that specifically bind to the extracellular domain of EGFR. EGFR-targeted monoclonal antibodies are not always effective against EGFR-expressing tumors. One approach taken with the aim of improving anti-EGFR antibody efficacy has been to develop mixtures of anti-EGFR monoclonal antibodies (i.e., oligoclonal antibodies) targeted to different sites (epitopes) on to the extracellular domain of EGFR. See, e.g., PCT Int. Pub. No. WO/2011/140254 and U.S. Pat. No. 7,887,805. These developments have created a need to enable the identification of cancer patients whose tumors have characteristics rendering them unresponsive to monoclonal anti-EGFR antibodies so that such patients may receive effective treatment via administration of oligoclonal anti-EGFR antibodies. The present disclosure answers this need and provides other benefits.

SUMMARY

Provided herein are theranostic methods for predicting responsiveness of tumor cells that express EGFR to therapeutic agents comprising anti-EGFR antibodies, and methods based on such predictions for treating patients having such tumors with such therapeutic agents. Anti-EGFR antibodies such as those monoclonal and oligoclonal antibodies described in PCT Int. Pub. No. WO/2011/140254 and corresponding pending U.S. patent application Ser. No. 13/100,920, in pending U.S. provisional patent applications Nos. 61/504,633 and 61/558,945, and in U.S. Pat. No. 7,887,805 (the "Oligoclonal Applications"), as well as oligoclonal mixtures of such antibodies in combination with other anti-EGFR antibodies, are useful for treatment of cancers, e.g., malignant (neoplastic) tumors. Examples of cancers include but are not limited to, carcinoma, adenoma, blastoma, sarcoma, and lymphoma. More particular examples of such cancers include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulvar cancer, thyroid cancer, hepatic carcinoma and various types of head and neck cancer. In a particular embodiment, a cancer treated or diagnosed using the methods disclosed herein is selected from melanoma, breast cancer, ovarian cancer, renal carcinoma, gastrointestinal/colon cancer, lung cancer (e.g., NSCLC), and prostate cancer.

Accordingly, theranostic methods predicting which tumors (e.g., malignant tumors) will be responsive to treatment with oligoclonal anti-EGFR antibodies, but not responsive to treatment with single monoclonal anti-EGFR antibodies, are provided. Also provided are kits useful for predicting responsiveness of tumors to anti-EGFR monoclonal and oligoclonal antibodies and methods of use thereof.

In one aspect, a preparation comprising only a single species of anti-EGFR monoclonal antibody (as opposed to preparations comprising mixtures of monoclonal antibodies) is provided for use in treating a patient having a tumor (e.g., a malignant tumor) that is predicted to have a favorable outcome (as described below) as a result of treatment #1, i.e., treatment with the preparation comprising only a single species of monoclonal antibody, and as a result of treatment #2, i.e., treatment with an oligoclonal anti-EGFR antibody preparation comprising a plurality of species of monoclonal anti-EGFR antibodies, one against each of at least two extracellular epitopes of EGFR, one of which antibody against at least two extracellular epitopes of EGFR being an antibody that inhibits ligand binding to EGFR. In another aspect, a preparation comprising a plurality of species of monoclonal anti-EGFR antibodies is provided for use in treating a patient having a tumor that is predicted to have a favorable outcome as a result of treatment #2, but not as a result of treatment #1.

Identification of tumors predicted to respond to treatment #1 and treatment #2, or to treatment #2, but not to treatment #1, comprises obtaining a biopsy sample of the tumor and:

a) measuring levels in the sample of at least two (e.g., at least three or at least four) low affinity EGFR ligands, e.g., selected from amphiregulin, epigen, or epiregulin, which may, for each ligand independently, be measured as levels of ligand protein or as levels of the corresponding RNA species coding for the ligand protein, in the biopsy sample, b) measuring levels in the sample of at least two (e.g., at least three) high affinity EGFR ligands, e.g., selected from betacellulin, EGF, HB-EGF or TGFα, which may, for each ligand independently, be measured as protein levels or as levels of the corresponding RNA species coding for them, in the biopsy sample, in one embodiment, all of the levels measured in a) are protein levels and all of the levels measured in b) are protein levels; in another embodiment all of the levels measured in a) are mRNA levels and all of the levels measured in b) are mRNA levels.

and, c) comparing the average level of each of the high affinity EGFR ligands, or of each corresponding RNA species, measured in a) to the average level of each of the low affinity EGFR ligands, or of each corresponding RNA species measured in b)

where if the average level of low affinity EGFR ligands, or RNAs coding for them, measured in a) is greater than the average level of high affinity EGFR ligands, or RNAs coding for them, measured in b), the patient is predicted to have the favorable outcome as a result of treatment #1, as well as as a result of treatment #2, and if the average level of low affinity EGFR ligands, or RNAs coding for them, measured in a) is less than or equal to the average level of high affinity EGFR ligands, or RNAs coding for them, measured in b), the patient is predicted to have an unfavorable outcome from treatment #1, but is predicted to have a favorable outcome from treatment #2.

In one embodiment, the at least two low affinity EGFR ligands is at least three low affinity ligands and the at least two high affinity EGFR ligands is three high affinity ligands. In another embodiment, the at least two low affinity EGFR ligands is four low affinity ligands and the at least two high affinity EGFR ligands is three high affinity ligands. In another embodiment, the at least two high affinity EGFR ligands is three high affinity ligands. In another embodiment, the at least two low affinity EGFR ligands is four low affinity ligands and the at least two high affinity EGFR ligands is at least two high affinity ligands.

In one embodiment, a monoclonal antibody preparation comprising only a single species of monoclonal antibody is provided for use in the treatment of a patient predicted to have a favorable outcome from treatment with either of the monoclonal anti-EGFR antibody preparation or the oligoclonal anti-EGFR antibody preparation and the patient is subsequently treated with the monoclonal preparation. In another embodiment, this patient is subsequently treated with the oligoclonal anti-EGFR antibody preparation.

In yet another embodiment, if the patient is predicted to have an unfavorable outcome from treatment with the monoclonal anti-EGFR antibody preparation, the patient is subsequently treated with the oligoclonal anti-EGFR antibody preparation.

The monoclonal anti-EGFR antibody preparation comprises a single monoclonal antibody that may be selected from, e.g., cetuximab, zalutumumab, nimotuzumab, matuzumab and panitumumab, all of which block ligand binding to EGFR, and therefore bind to the same or overlapping EGFR epitopes (Bin 1) and are not suitable for use together in oligoclonal antibody preparations. Members of the plurality of anti-EGFR antibody species in an oligoclonal preparation separately and uniquely bind to two different extracellular epitopes of EGFR, may separately and uniquely bind to at least three extracellular epitopes of EGFR (in some cases no more than three). Such a plurality may comprise two or three different species of monoclonal anti-EGFR antibodies, and in some embodiments no more than three different species. Mixtures comprising more than one antibody against any one epitope of EGFR are less preferred. In certain embodiments the oligoclonal preparations are duos, trios, or fourfold combinations of antibodies as disclosed in the Oligoclonal Applications. In other embodiments, the oligoclonal preparations provided herein comprise one or more of the anti-EGFR antibodies (e.g., of the above duos or trios or other oligoclonal combinations) that are not Bin 1 antibodies in combination with one of cetuximab, zalutumumab, nimotuzumab, matuzumab and panitumumab (which are all Bin 1 antibodies).

In another embodiment, if the patient is predicted to have an unfavorable outcome from treatment with the monoclonal anti-EGFR antibody preparation, the patient is subsequently treated with combination therapy comprising separate administration of at least two different monoclonal anti-EGFR antibodies. In certain aspects, the at least two different monoclonal anti-EGFR antibodies are selected from any of the anti-EGFR antibodies disclosed in the Oligoclonal Applications, as well as from cetuximab, zalutumumab, nimotuzumab, matuzumab and panitumumab, provided that one of the anti-EGFR antibodies is an antibody that inhibits ligand binding to EGFR.

In another embodiment the tumor is a tumor of the skin, central nervous system, head, neck, esophagus, stomach, colon, rectum, anus, liver, pancreas, bile duct, gallbladder, lung, breast, ovary, uterus, cervix, vagina, testis, germ cells, prostate, kidney, ureter, urinary bladder, adrenal, pituitary, thyroid, bone, muscle or connective tissue.

In another aspect, a method of treating a tumor in a patient by administration of a monoclonal anti-EGFR antibody preparation comprising a single species of monoclonal antibody is provided, the method comprising, prior to the administration, determining that the tumor does not have a level of high affinity ligands that is equal to or greater than the level of low affinity ligands in the tumor and not administering the monoclonal preparation if the tumor does have a level of high affinity ligands that is equal to or greater than the level of low affinity ligands in the tumor.

In another aspect, a method of treating a tumor in a patient by administration of an oligoclonal anti-EGFR antibody preparation comprising a plurality of species of monoclonal anti-EGFR antibodies, one against each of at least two extracellular epitopes of EGFR, one of the species of monoclonal anti-EGFR antibody inhibiting the binding of ligand to EGFR, is provided, the method comprising, prior to the administration, determining that the tumor has a level of high affinity ligands that is equal to or greater than the level of low affinity ligands in the tumor. In one embodiment, the oligoclonal anti-EGFR antibody preparation is MM-151.

Also provided are kits for testing a tumor biopsy sample to determine levels of both high and low affinity EGFR ligands in the sample, said kits being comprised by one or more containers comprising;

a) at least two pairs of high affinity EGFR ligand-specific polymerase chain reaction (PCR) primers, b) at least two pairs of low affinity EGFR ligand-specific PCR primers, and c) at least one reverse transcription PCR (RT-PCR) reagent.

In one embodiment the at least two pairs of high affinity EGFR ligand-specific polymerase chain reaction primers are specific to at least two of betacellulin, EGF, HB-EGF or TGFα and each of the at least two pairs of low affinity EGFR ligand-specific polymerase chain reaction primers are specific to at least two of amphiregulin, epigen, or epiregulin. In another embodiment the at least two pairs of high affinity EGFR ligand-specific primers consist of all of betacellulin, EGF, HB-EGF and TFGα and the at least two pairs of high affinity EGFR ligand-specific primers consist of all of amphiregulin, epigen, and epiregulin. In another embodiment the kit comprises at least one fluorescent reporter molecule suitable for use in a real-time RT-PCR assay. In yet another embodiment the at least one RT-PCR reagent is one or more of an RNA-dependent DNA polymerase, a DNA-dependent DNA polymerase, a buffer, or a solution comprising at least micromolar concentrations of each of adenosine triphosphate (ATP), guanosine triphosphate (GTP), cytidine triphosphate (CTP), and thymidine triphosphate (TTP). In a further embodiment the one or more containers comprises either or both of at least one container that has an internal temperature of below 20° C. and above 0° C., and at least one container that has an internal temperature of below 0° C. Preferably the contents of all, or at least one, of the at least one container has been prepared under cGMP conditions.

In another aspect, a method is provided for treating a patient having a cancerous tumor, the method comprising determining, according to any of the methods described above, if the patient is predicted to have the favorable outcome as a result of treatment #1 and as a result of treatment #2 or if the patient is predicted to have the favorable outcome as a result of treatment #2 but not as a result of treatment #1, wherein if the patient is predicted to have a favorable outcome as a result of treatment #1 and as a result of treatment #2, the patient is treated with treatment #1 or treatment #2; and if the patient is predicted to have a favorable outcome as a result of treatment #2 but not as a result of treatment #1, the patient is treated with treatment 2 and not with treatment #1. Determining whether the patient will have a favorable outcome may be accomplished by use of any of the theranostic methods described above, which may be accomplished by use of a kit described above.

In certain aspects of the above methods, the oligoclonal anti-EGFR antibody preparation is a composition comprising a trio of anti-EGFR antibodies comprising a first antibody, a second antibody and a third antibody, wherein (i) the first antibody is, or competes for binding to EGFR with, or binds to the same epitope as, an antibody selected from the group consisting of ca, cb and cc; (ii) the second antibody is, or competes for binding to EGFR with, or binds to the same epitope as, an antibody selected from the group consisting of cd, ce and cf; and (iii) the third antibody is, or competes for binding to EGFR with, or binds to the same epitope as, an antibody selected from the group consisting of cg, ch, ci, cj and ck, wherein ca, cb, cd, ce, cf, cg, ch, ci, cj, and ck are each disclosed in PCT Int. Pub. No. WO/2011/140254 and corresponding pending U.S. patent application Ser. No. 13/100, 920.

Other features and advantages of the invention will be apparent from the following detailed description, and from the claims.

BRIEF DESCRIPTION OF THE FIGURES

FIG. 1A shows inhibition of ERK activation by the Bin1/2 antibodies cb and cd. FIG. 1B shows the inhibition of EGFR activation by the Bin1/2 antibodies and cd. FIG. 1C shows the inhibition of ERK activation by the Bin1/3 antibodies cb and ch. Lines depict a five parameter logistic fit to the data from each combination.

DETAILED DESCRIPTION

I. Definitions

Figure 1A:
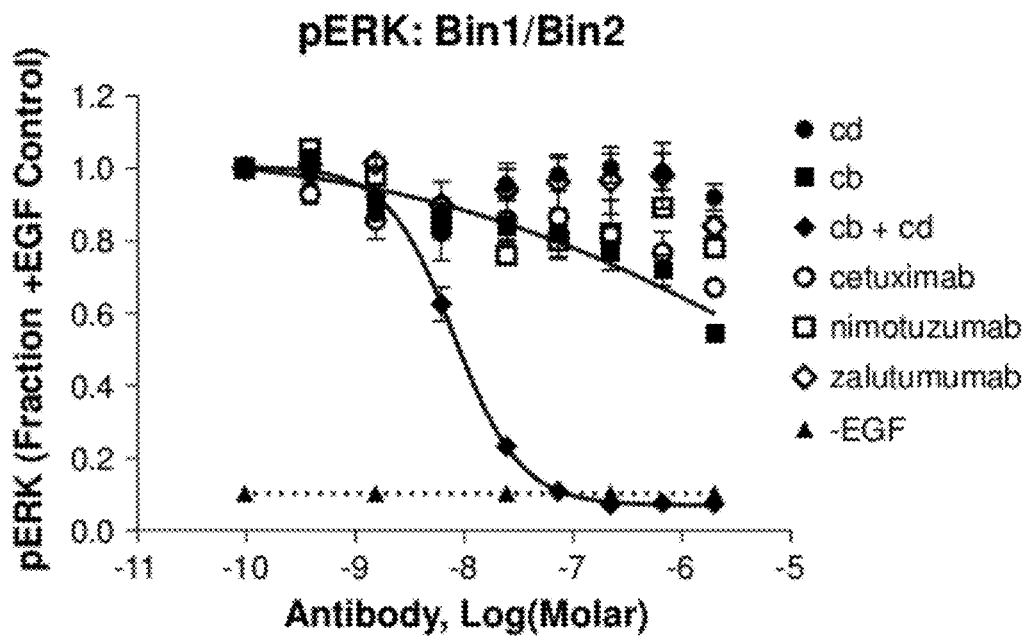
FIGS. 1A-1C: Phospho-EGF receptor and phospho-ERK signaling inhibition by single and pairwise combinations of Bin 1+Bin 2 or Bin 1+Bin 3 antibodies and comparisons with other known anti-EGFR antibodies such as cetuximab, nimotuzumab, and zalutumumab.

The terms "EGFR," and "EGF receptor" are used interchangeably herein to refer to human EGFR protein (also referred to as ErbB1 or HER1); see UniProtKB/Swiss-Prot entry P00533.

The term "monoclonal antibody" as used herein refers to an antibody obtained from a population of substantially homogeneous antibodies, i.e., the individual antibodies comprising the population are identical except for possible naturally occurring mutations that may be present in minor amounts. Such antibodies may be obtained, e.g. from hybridomas or by recombinant expression. Antigen binding fragments (including scFvs) of such immunoglobulins are also encompassed by the term "monoclonal antibody" as used herein. Monoclonal antibodies are highly specific, generally being directed against a single epitope on a single antigen site, e.g., on the extracellular domain of EGFR. Monoclonal antibodies include chimeric antibodies—whose variable regions derive from a first animal species (e.g., mouse) and whose constant regions derive from a second animal species (e.g., human), human antibodies and humanized antibodies.

The terms "treat," "treating," and "treatment," as used herein, refer to therapeutic or preventative measures described herein. The methods of "treatment" employ administration to a subject, an antibody or antibody pair or trio disclosed herein, for example, a subject having a disorder associated with EGFR dependent signaling or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

Commercially available pharmaceutical anti-EGFR antibodies include cetuximab, panitumumab and nimotuzumab (which is not yet available in the US market). Other pharmaceutical anti-EGFR antibodies include zalutumumab, and matuzumab, which are in development. Still other anti-EGFR antibodies include those disclosed in the Oligoclonal Applications, e.g., the antibodies disclosed below.

P1X is a human IgG1 having a heavy chain variable region comprising SEQ ID NO: 1 and a light chain variable region comprising SEQ ID NO: 2;

P2X is a human IgG1 having a heavy chain variable region comprising SEQ ID NO: 3 and a light chain variable region comprising SEQ ID NO: 4; and P3X is a human IgG1 having a heavy chain variable region comprising SEQ ID NO: 5 and a light chain variable region comprising SEQ ID NO: 6.

"MM-151" indicates a triple combination of P1X+P2X+P3X at a P1X:P2X:P3X molar ratio of 2:2:1.

TABLE 1

Exemplary Antibodies

| | | |
|---|---|---|
| P1X $V_H$ | MGFGLSWLFLVAILKGVQC QVQLVQSGAEVKKPGSSVKV SCKASGGTFSSYAISWVRQA PGQGLEWMGSIIPIFGTVNY AQKFQGRVTITADESTSTAY MELSSLRSEDTAVYYCARDP SVNLYWYFDLWGRGTLVTVSS | SEQ ID NO: 1 |
| P1X $V_L$ | MGTPAQLLFLLLLWLPDTTG DIQMTQSPSTLSASVGDRVT ITCRASQSISSWWAWYQQKP GKAPKLLIYDASSLESGVPS RFSGSGSGTEFTLTISSLQP DDFATYYCQQYHAHPTTFGG GTKVEIK | SEQ ID NO: 2 |
| P2X $V_H$ | MGFGLSWLFLVAILKGVQC QVQLVQSGAEVKKPGSSVKV SCKASGGTFGSYAISWVRQA PGQGLEWMGSIIPIFGAANP AQKSQGRVTITADESTSTAY MELSSLRSEDTAVYYCAKMG RGKVAFDIWGQGTMVTVSS | SEQ ID NO: 3 |
| P2X $V_L$ | MGTPAQLLFLLLLWLPDTTG DIVMTQSPDSLAVSLGERAT INCKSSQSVLYSPNNKNYLA WYQQKPGQPPKLLIYWASTR ESGVPDRFSGSGSGTDFTLT ISSLQAEDVAVYYCQQYYGS PITFGGGTKVEIK | SEQ ID NO: 4 |
| P3X $V_H$ | MGFGLSWLFLVAILKGVQC QVQLVQSGAEVKKPGASVKV SCKASGYAFTSYGINWVRQA PGQGLEWMGWISAYNGNTYY AQKLRGRVTMTTDTSTSTAY MELRSLRSDDTAVYYCARDL GGYGSGSVPFDPWGQGTLVTV SS | SEQ ID NO: 5 |
| P3X $V_L$ | MGTPAQLLFLLLLWLPDTTG EIVMTQSPATLSVSPGERAT LSCRASQSVSSNLAWYQQKP GQAPRLLIYGASTRATGIPA RFSGSGSGTEFTLTISSLQS EDFAVYYCQDYRTWPRRVFG GGTKVEIK | SEQ ID NO: 6 |
| zalutumumab $V_H$ | QVQLVESGGGVVQPGRSLRLSC AASGFTFSTYGMHWVRQAPGKG LEWVAVIWDDGSYKYYGDSVKG RFTISRDNSKNTLYLQMNSLRA EDTAVYYCARDGITMVRGVMKD YFDYWGQGTLVTVSS | SEQ ID NO: 7 |
| zalutumumab $V_L$ | AIQLTQSPSSLSASVGDRVTIT CRASQDISSALVWYQQKPGKAP KLLIYDASSLESGVPSRFSGSE SGTDFTLTISSLQPEDFATYYC QQFNSYPLTFGGGTKVEIK | SEQ ID NO: 8 |
| Nimotuzumab $V_H$ | QVQLQQPGAELVKPGASVKLSC KASGYTFTNYYIYWVKQRPGQG LEWIGGINPTSGGSNFNEKFKT KATLTVDESSTTAYMQLSSLTS EDSAVYYCTRQGLWFDSDGRGF DFWGQGTTLTVSS | SEQ ID NO: 9 |
| Nimotuzumab $V_L$ | DVLMTQIPLSLPVSLGDQASIS CRSSQNIVHSNGNTYLDWYLQK PGQSPNLLIYKVSNRESGVPDR FRGSGSGTDFTLKISRVEAEDL GVYYCFQYSHVPWTFGGGTKLE IK | SEQ ID NO: 10 |

The term "patient" includes human and other mammalian subjects that receive either prophylactic or therapeutic treatment.

The term "sample" refers to tissue, body fluid, or a cell (or a fraction of any of the foregoing) taken from a patient. Normally, the tissue or cell will be removed from the patient, but in vivo diagnosis is also contemplated. In the case of a solid tumor, a tissue sample can be taken from a surgically removed tumor and prepared for testing by conventional techniques. In the case of lymphomas and leukemias, lymphocytes, leukemic cells, or lymph tissues can be obtained (e.g., leukemic cells from blood) and appropriately prepared. Other samples, including urine, tears, serum, plasma, cerebrospinal fluid, feces, sputum, cell extracts etc. can also be useful for particular cancers.

Various aspects of the disclosure are described in further detail in the following subsections.

II. Outcomes

A patient having a tumor predicted by the methods disclosed herein to have a favorable outcome following treatment with a monoclonal or oligoclonal anti-EGFR antibody, and who is then treated accordingly, may exhibit one of the following responses to therapy:

Pathologic complete response (pCR): absence of invasive cancer following primary systemic treatment.

Complete Response (CR): Disappearance of all target lesions.

Partial Response (PR): At least a 30% decrease in the sum of dimensions of target lesions, taking as reference the baseline sum diameters; or Stable Disease (SD): Neither sufficient shrinkage to qualify for partial response, nor sufficient increase to qualify for progressive disease, taking as reference the smallest sum diameters while on study.

In exemplary outcomes, patients treated as disclosed herein may experience improvement in at least one sign of cancer.

In one embodiment the patient so treated exhibits pCR, CR, PR, or SD.

In another embodiment, the patient so treated experiences tumor shrinkage and/or decrease in growth rate, i.e., suppression of tumor growth. In another embodiment, unwanted cell proliferation is reduced or inhibited. In yet another embodiment, one or more of the following can occur: the number of cancer cells can be reduced; tumor size can be reduced; cancer cell infiltration into peripheral organs can be inhibited, retarded, slowed, or stopped; tumor metastasis can be slowed or inhibited; tumor growth can be inhibited; recurrence of tumor can be prevented or delayed; one or more of the symptoms associated with cancer can be relieved to some extent.

In other embodiments, such improvement is measured by a reduction in the quantity and/or size of measurable tumor lesions. Measurable lesions are defined as those that can be accurately measured in at least one dimension (longest diameter is to be recorded) as >10 mm by CT or MRI scan (e.g., CT scan slice thickness no greater than 5 mm), 10 mm caliper measurement by clinical exam or >20 mm by chest X-ray. The size of non-target lesions can also be measured for improvement. In one embodiment, lesions can be measured on x-rays or CT or MRI images.

In other embodiments, cytology or histology can be used to evaluate responsiveness to a therapy. The cytological confirmation of the neoplastic origin of any effusion that appears or worsens during treatment when the measurable tumor has met criteria for response or stable disease can be considered to differentiate between response or stable disease (an effusion may be a side effect of the treatment) and progressive disease.

In some embodiments, a beneficial response to therapy is indicated by at least one therapeutic effect selected from the group consisting of reduction in size of a tumor, reduction in number of metastatic lesions appearing over time, complete remission, partial remission, stable disease, increase in overall response rate, or a pathologic complete response.

III. Pharmaceutical Compositions

Pharmaceutical compositions for use in the methods provided herein are commercially available anti-EGFR compositions, e.g., of cetuximab, panitumumab and nimotuzumab, as well as the various pharmaceutical compositions provided in the Oligoclonal Applications.

IV. Use of Oligoclonal Antibodies

Provided herein are methods of determining whether or not a monoclonal anti-EGFR antibody preparation comprising only a single species of anti-EGFR antibody should be used to treat a tumor. Use of oligoclonal anti-EGFR antibodies for the treatment of a disease associated with high-affinity EGFR ligand-driven signaling is also provided, as are methods of use of oligoclonal anti-EGFR antibodies for the treatment of tumor comprising protein or mRNA levels of at least two high-affinity EGFR ligands that are higher than levels in the tumor of at least two low-affinity EGFR ligands. Cancers treated in accordance with the methods provided include melanoma, breast cancer, ovarian cancer, renal carcinoma, gastrointestinal cancer, gastro-esophageal junction cancer, colon cancer, lung cancer, pancreatic cancer, skin cancer, head and neck cancer glioblastoma, prostate cancer and other solid and/or metastatic tumors.

The monoclonal or oligoclonal antibody can be administered alone or with another therapeutic agent that acts in conjunction with or synergistically with the oligoclonal antibody to treat the disease associated with EGFR-mediated signaling.

Also provided are kits for testing a tumor sample, e.g., a tumor biopsy sample or a circulating tumor cell, to determine levels of both high and low affinity EGFR ligands in the sample, said kits being comprised by one or more containers comprising;

a) at least two pairs of high affinity EGFR ligand-specific polymerase chain reaction (PCR) primers, b) at least two pairs of low affinity EGFR ligand-specific PCR primers, and c) at least one reverse transcription PCR (RT-PCR) reagent.

In another embodiment, the kit may further contain instructions for use in determining how to treat a tumor in a patient following determination of levels of high and low affinity ligands in a sample of the tumor. The kit may include an indication of the intended use of the contents of the kit (e.g., in the form of a label or other printed or recorded matter).

Other embodiments are described in the following non-limiting Examples.

The present invention is further illustrated by the following examples which should not be construed as further limiting. The contents of Sequence Listing, figures and all references, patents and published patent applications cited throughout this application are expressly incorporated herein by reference.

EXAMPLES

Materials and Methods

Throughout the examples, the following materials and methods are used unless otherwise stated.

In general, unless otherwise indicated, conventional techniques of chemistry, molecular biology, recombinant DNA technology, immunology (especially, e.g., antibody technology), and standard techniques in polypeptide preparation are used. See, e.g., Sambrook, Fritsch and Maniatis, Molecular Cloning Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., C.S.H.L. Press, Pub. (1999); and Current Protocols in Molecular Biology, eds. Ausubel et al., John Wiley & Sons (1992).

Pulverization of Tumor Cells

A cryopulverizer (COVARIS Inc.) is used for the pulverization of tumors. Tumors are stored in special bags (pre-weighed before the addition of the tumor) and placed in liquid nitrogen while handling them. For small tumors, 200 µL of Lysis buffer is first added to the bag containing the tumor, frozen in liquid nitrogen and then pulverized to improve the recovery of the tumor from the bag. Pulverized tumors are transferred to 2 mL EPPENDORF tubes and placed in liquid nitrogen until ready for further processing.

Lysis of Tumor Cells

Tumors are lysed in Lysis buffer supplemented with protease and phosphatase inhibitors. Lysis Buffer is added to the tumor aliquots in a final concentration of about 62.5 mg/mL. Tumor samples are homogenized by vortexing for 30 sec and incubating on ice for about 30 min. The lysates are spun for about 10 min in Qiagen QIASHREDDER columns for further homogenization of the samples. Cleared lysates are aliquoted into fresh tubes for further processing.

Measurement of Inhibition of EGFR Ligand-Mediated phosphorylation of ERK in Tumor Cells Inhibition of ligand-mediated tumor cell signaling is investigated as follows: A431 (ATCC CRL-1555™) epidermoid carcinoma cells are seeded at a density of 35,000 cells/well or 17,500 cells per half well in 96 well tissue culture plates and grown in DMEM medium supplemented with antibiotics, 2 mM L-glutamine and 10% fetal bovine serum (FBS) for 24 hours at 37° C. and 5% carbon dioxide. Cells are serum starved in 1% FBS medium with antibiotics and 2 mM L-glutamine for about 20 hours at 37° C. and 5% carbon dioxide. Cells are then treated as described below in each Example. Cells are washed with ice-cold PBS and lysed in 50 µl ice-cold Lysis buffer (Mammalian Protein Extraction Lysis Reagent (M-PER, Pierce, Thermo Scientific product #78505) amended with 150 mM NaCl and protease inhibitor cocktail (Sigma, P714)) by incubating on ice for 30 minutes. Lysates are either analyzed immediately by ELISA for phospho-ERK (a downstream effector of EGFR) or frozen at −80° C. until use.

ELISA Assays

For the phospho-EGFR sandwich ELISA, 96-half well GREINER high binding plates (Cat. #675077; GREINER BIO-ONE, Monroe, N.C.) are coated with 50 µL of an EGFR antibody (4 µg/ml final concentration; EGFR Ab-11, Clone: 199.12, without BSA and azide, Fisher Scientific, cat#MS396P1ABX), and incubated overnight at room temperature. Next morning, plates are washed 3 times with 100 µl/well PBST (0.05% Tween-20) on a BIOTEK plate washer. Plates are subsequently blocked for about 1 hour at room temperature with 2% BSA in PBS. The plates are washed 3 times with 100 µl/well PBST (0.05% Tween-20) on the BIOTEK plate washer. Cell lysates (50 µl) or standards (pEGFR pY1068 ELISA kit, R&D Systems, cat#DYC3570) diluted in 50% Lysis buffer and 1% BSA-PBS (per the manufacturer's recommendations) are added to the plates in duplicates and incubated for 2 hrs at room temperature or overnight at 4° C. with shaking. Plates are then washed 3 times with 100 µl/well in the BIOTEK plate washer with PBST (PBS with 0.05% Tween-20). About 50 µl of a detection antibody (pEGFR pY1068 ELISA kit, R&D Systems, cat# DYC3570) conjugated to horseradish peroxidase (HRP) diluted (as per manufacturer's instructions) in 2% BSA, PBS is added and incubated for about 2 hour at room temperature. The plate is washed 3 times with 100 µl/well in the BIOTEK plate washer with PBST (0.05% Tween-20). About 50 µL of SUPERSIGNAL PICO ELISA substrate is added and the plate is read using an Envision (Perkin Elmer) plate reader. The data are analyzed and duplicate samples are averaged and error bars are used to represent the standard deviation between the two replicates.

The phospho-ERK ELISA is performed similarly to the phospho-EGFR ELISA with the following changes: Human pERK ELISA DUOSET kit is purchased from R&D Systems (cat#DYC1018-5) and used as recommended by the manufacturer. The data are analyzed by subtracting background signal, regressing to a recombinant standard supplied by the manufacturer, and back-calculating the data (BCD) to correct for dilution factors. Duplicate samples are averaged and error bars are used when indicated to represent the standard deviation between two replicates.

Example 1

Figure 1B:
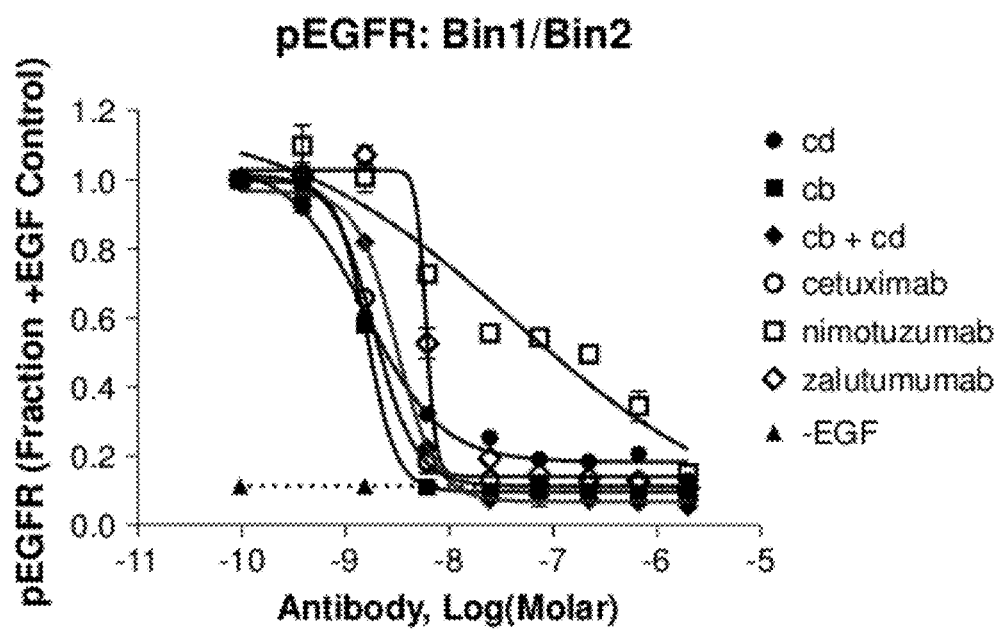
Figure 1C:
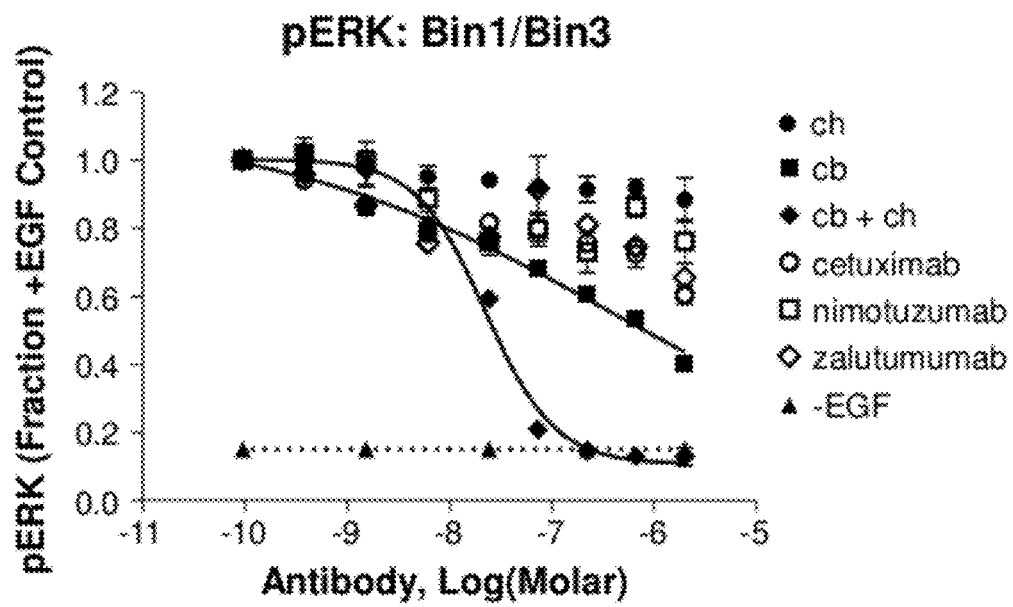
Figure 2A:
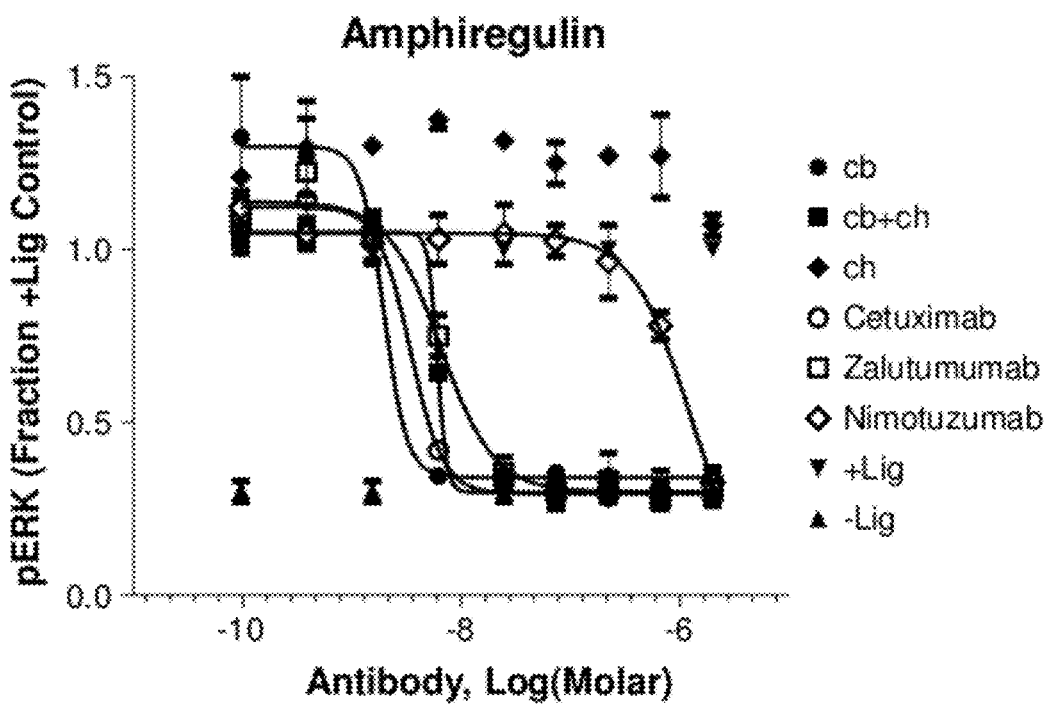
FIGS. 2A-2G: Inhibition of ligand-mediated tumor cell signaling in A431 cells preincubated with varying concentrations of anti-EGFR monoclonal antibodies cb (Bin1), cd (Bin2), cetuximab, zalutumumab, or nimotuzumab; as well as the oligoclonal combination of cb+cd; for 2 hrs. After incubation cells were stimulated with an EGFR ligand (8 nanomolar final concentration) for about 10 minutes. Figures show ELISA analysis of phospho-ERK (pERK) production (y-axis) as a function of antibody concentration (x-axis, in Log Molar concentration) after stimulation with the ligands amphiregulin (FIG. 2A), epigen (FIG. 2B), epiregulin (FIG. 2C), betacellulin (FIG. 2D), epidermal growth factor (EGF, FIG. 2E), heparin-binding EGF-like growth factor (HB-EGF, FIG. 2F), or transforming growth factor α (TGF-α, FIG. 2G). A431 cells incubated in the absence of anti-EGFR antibodies but with the ligand indicated in each graph (+Lig) or without ligand stimulation (−Lig) were used as positive and negative controls, respectively.
Figure 2B:
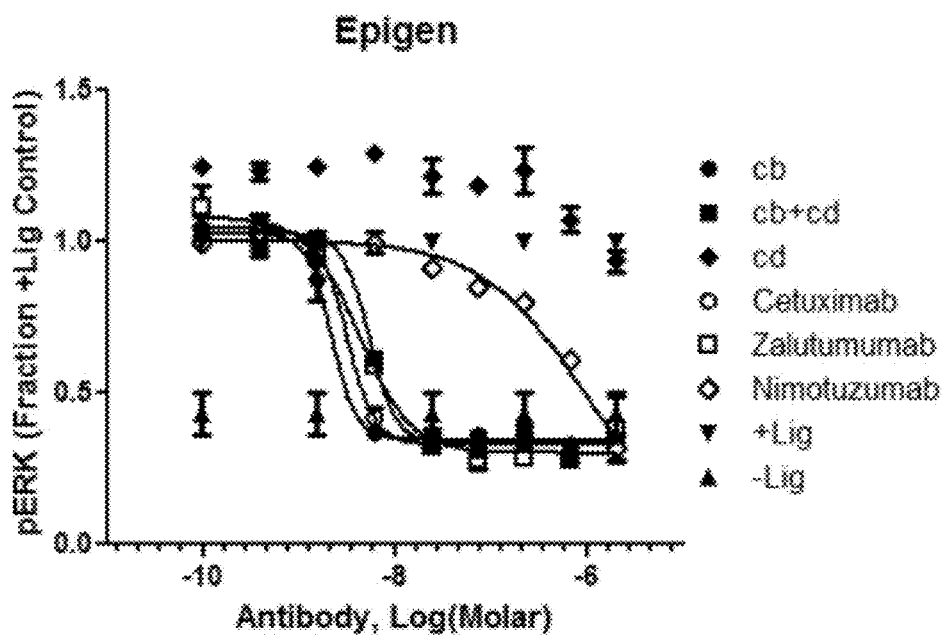
Figure 2C:
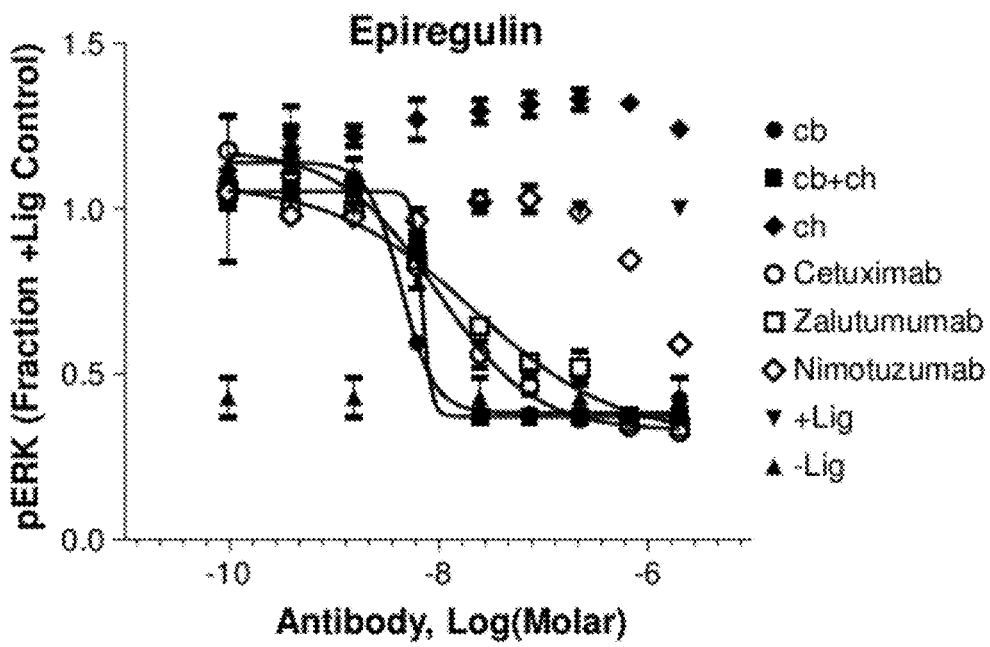
Figure 2D:
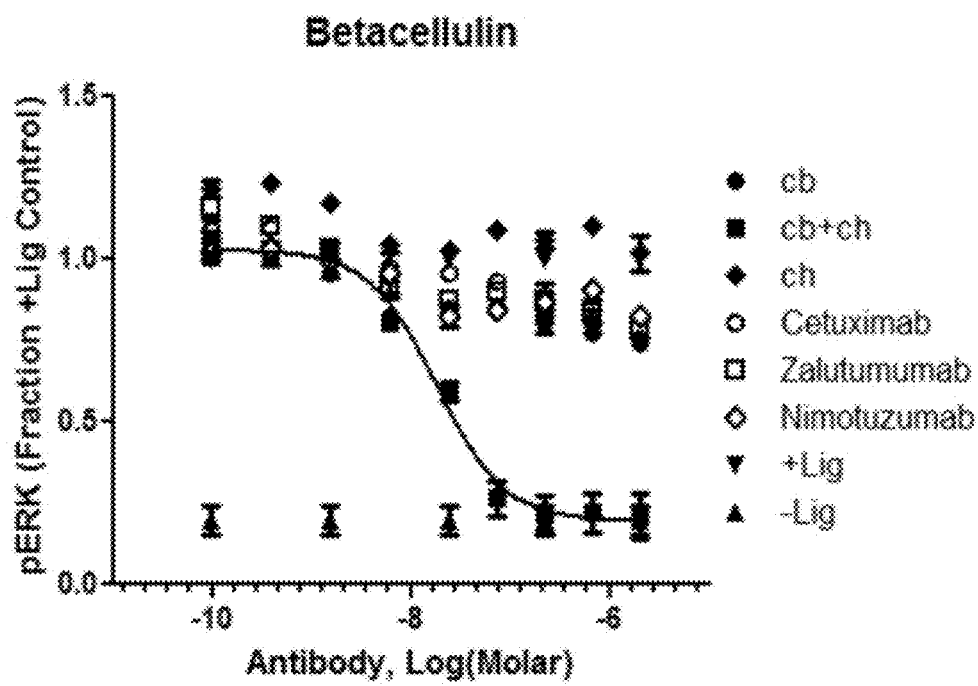
Figure 2E:
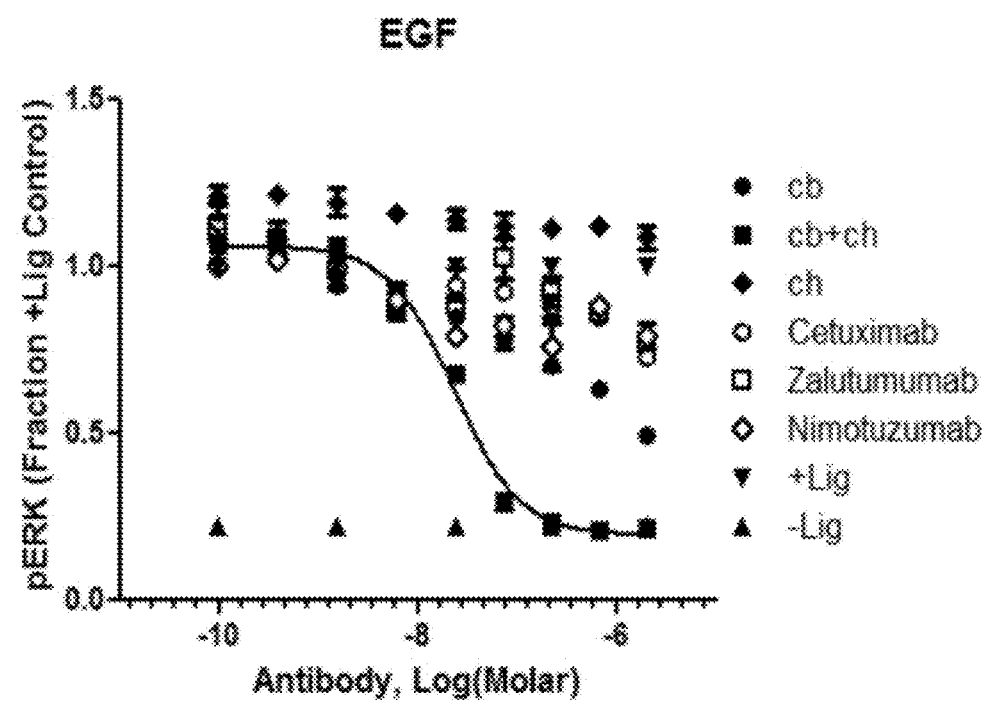
Figure 2F:
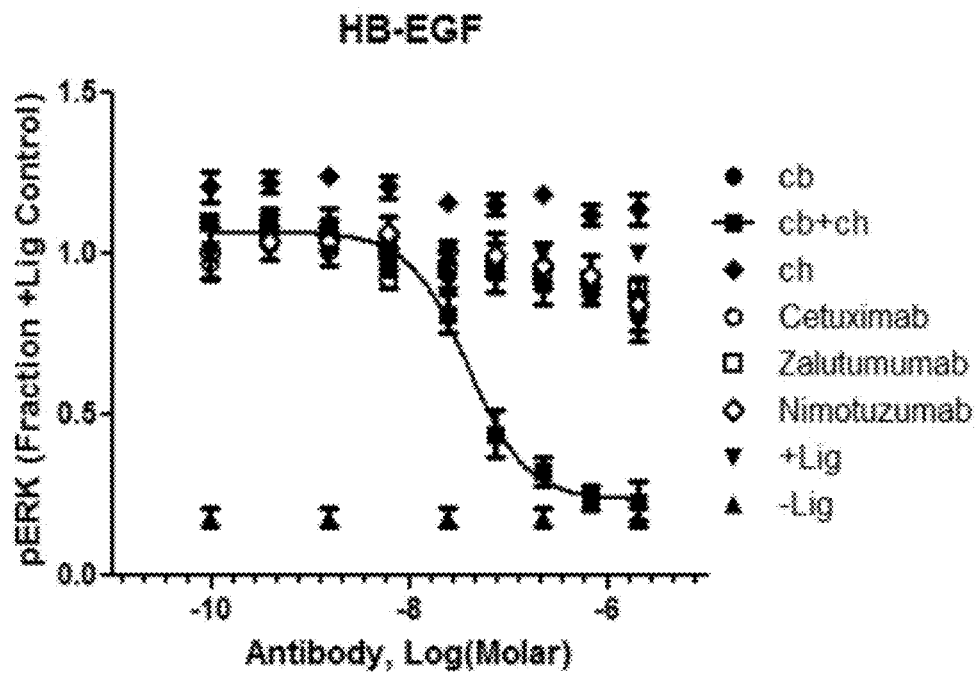
Figure 2G:
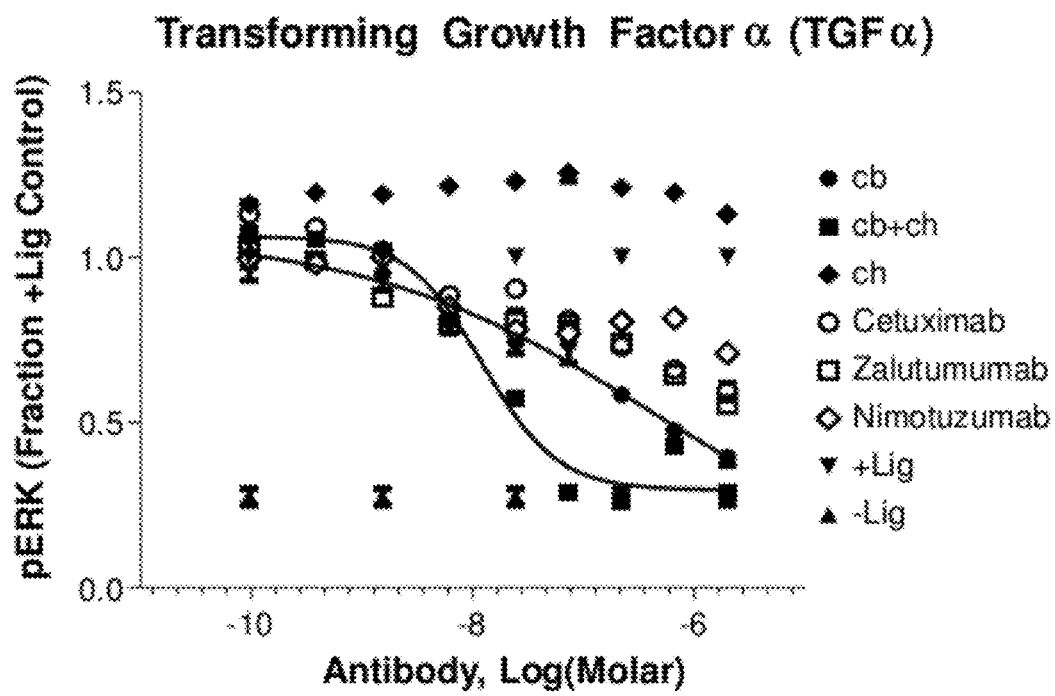
Figure 3A:
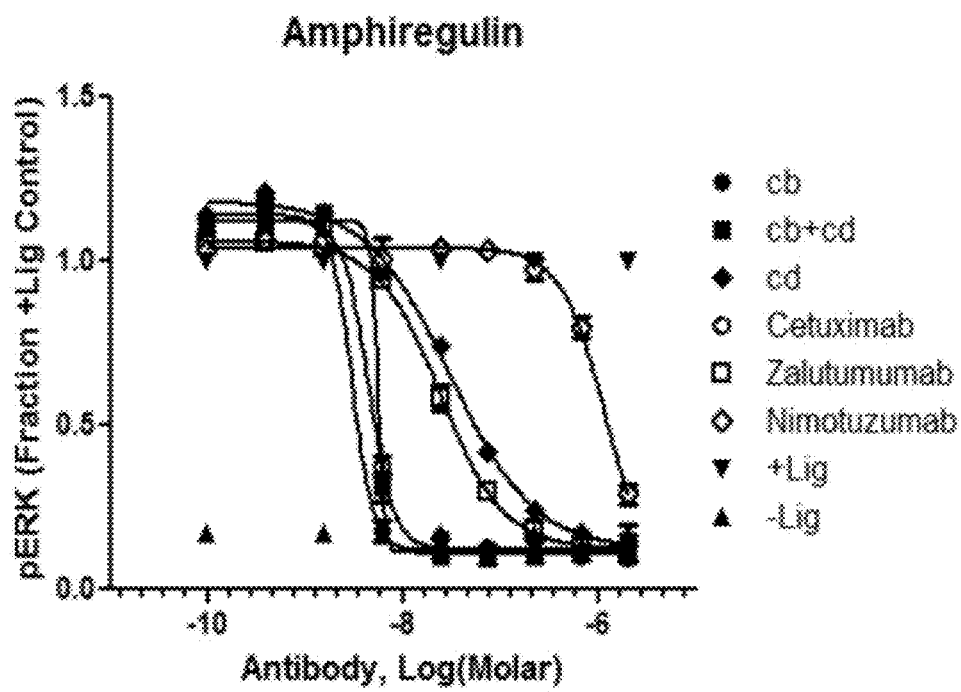
FIGS. 3A-3G: Inhibition of ligand-mediated tumor cell signaling in A431 cells preincubated with varying concentrations of anti-EGFR monoclonal antibodies cb (Bin1), ch (Bin3), cetuximab, zalutumumab, or nimotuzumab; as well as the oligoclonal combination of cb+ch; for 2 hrs. After pre-incubation with antibodies, cells were stimulated with an EGFR ligand (8 nanomolar final concentration) for 10 minutes. Figures show ELISA analysis of phospho-ERK (pERK) production (y-axis) as a function of antibody concentration (x-axis, in Log Molar concentration) after stimulation with the ligands amphiregulin (FIG. 3A), epigen (FIG. 3B), epiregulin (FIG. 3C), betacellulin (FIG. 3D), epidermal growth factor (EGF, FIG. 3E), heparin-binding EGF-like growth factor (HB-EGF, FIG. 3F), or transforming growth factor α (TGF-α, FIG. 3G). A431 cells incubated in the absence of anti-EGFR antibodies but with the ligand indicated in each graph (+Lig) or without ligand stimulation (−Lig) were used as positive and negative controls, respectively.
Figure 3B:
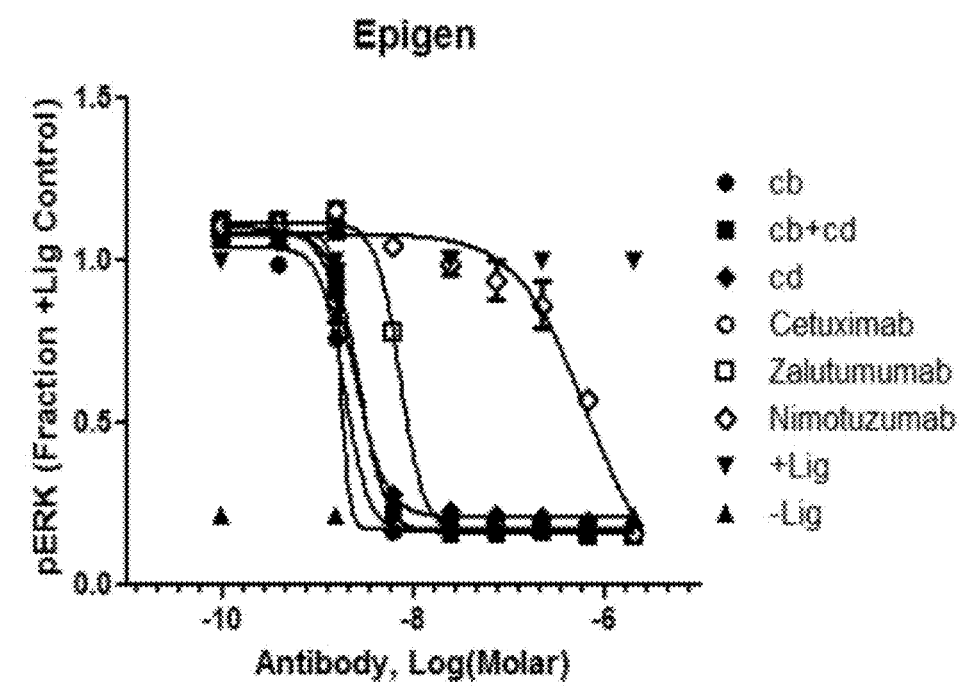
Figure 3C:
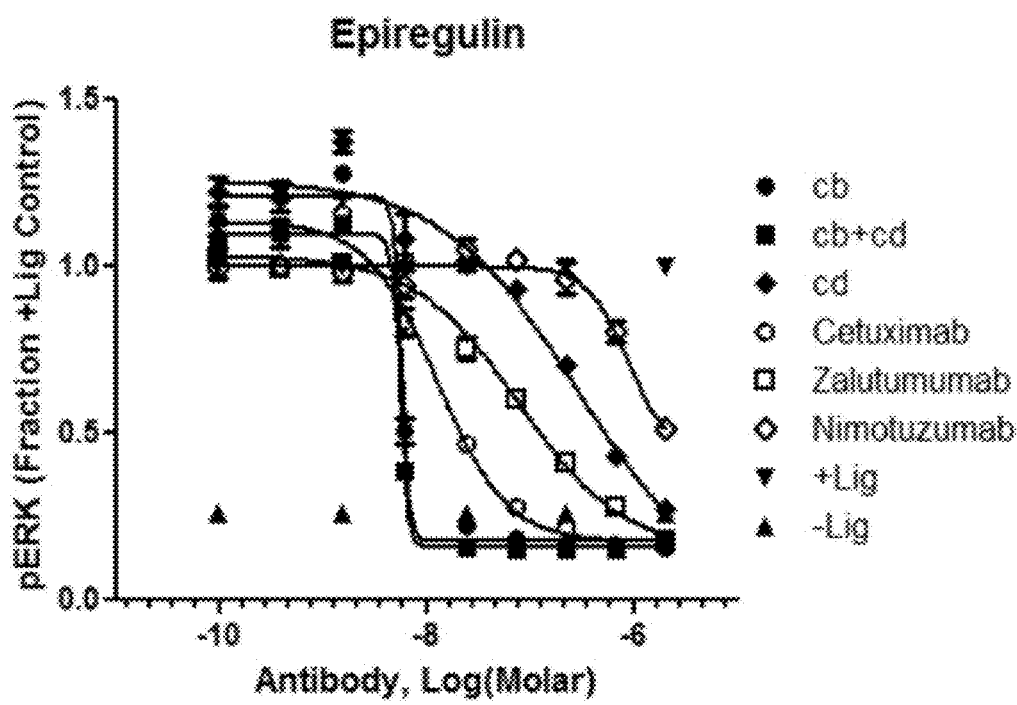
Figure 3D:
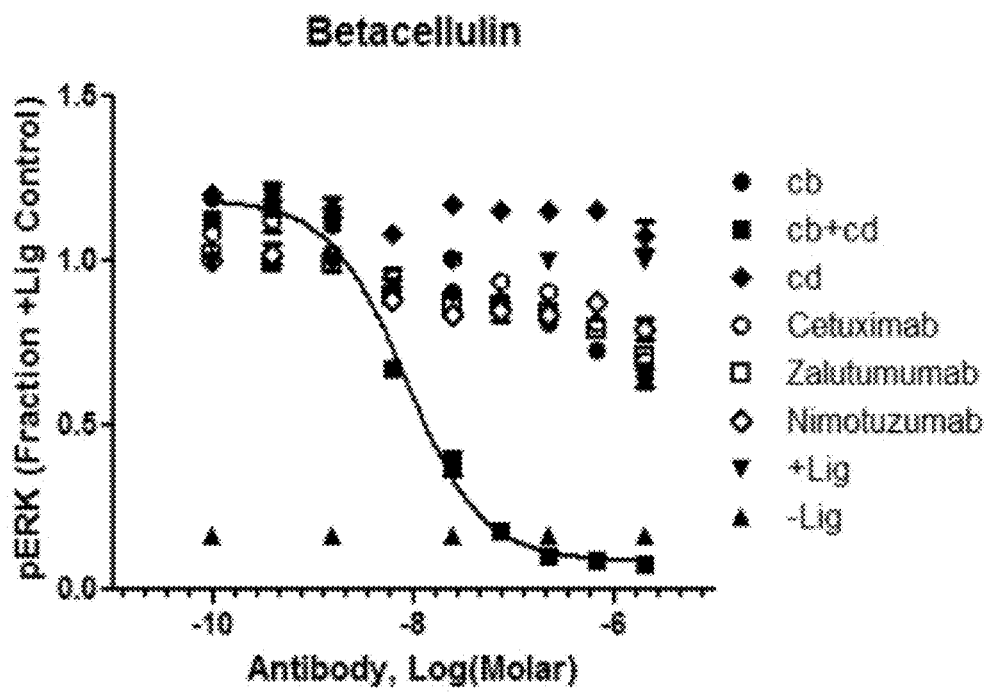
Figure 3E:
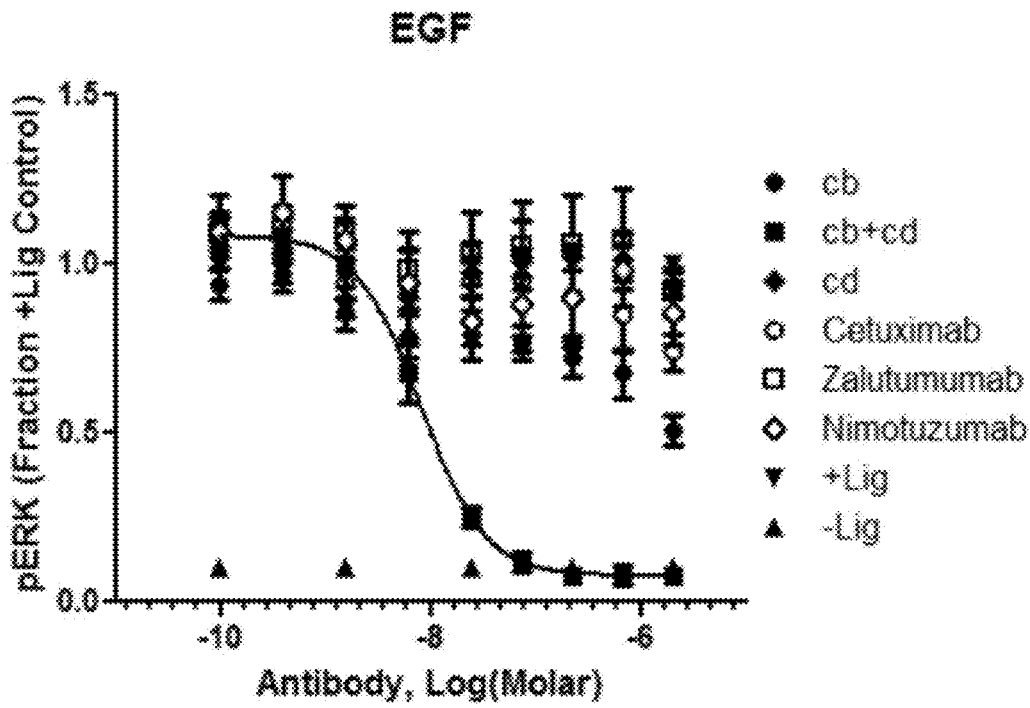
Figure 3F:
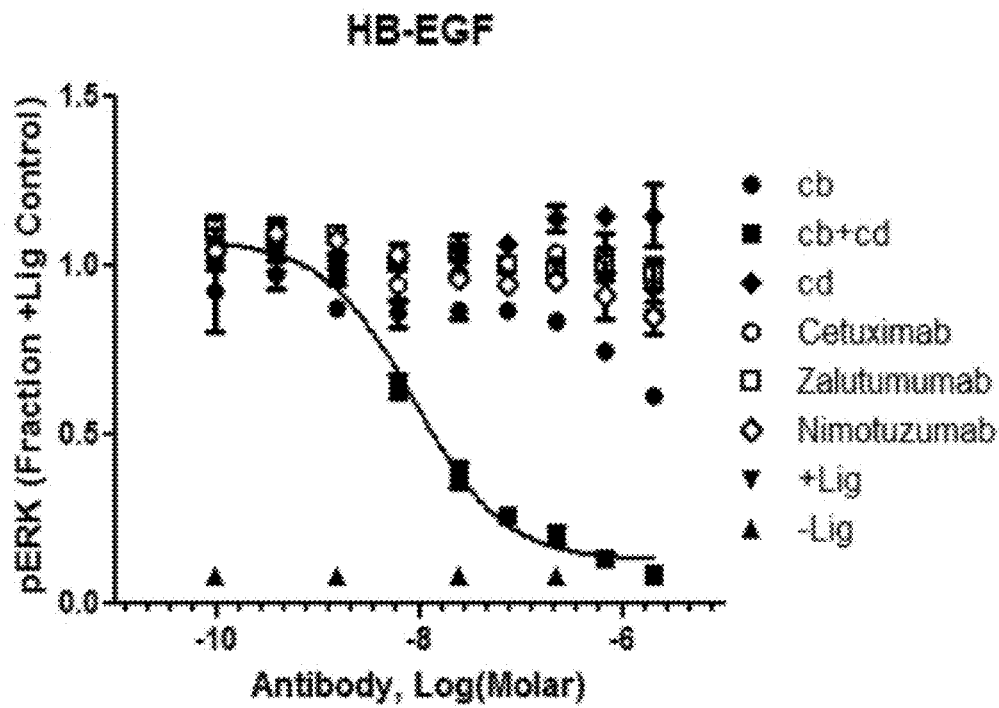
Figure 3G:
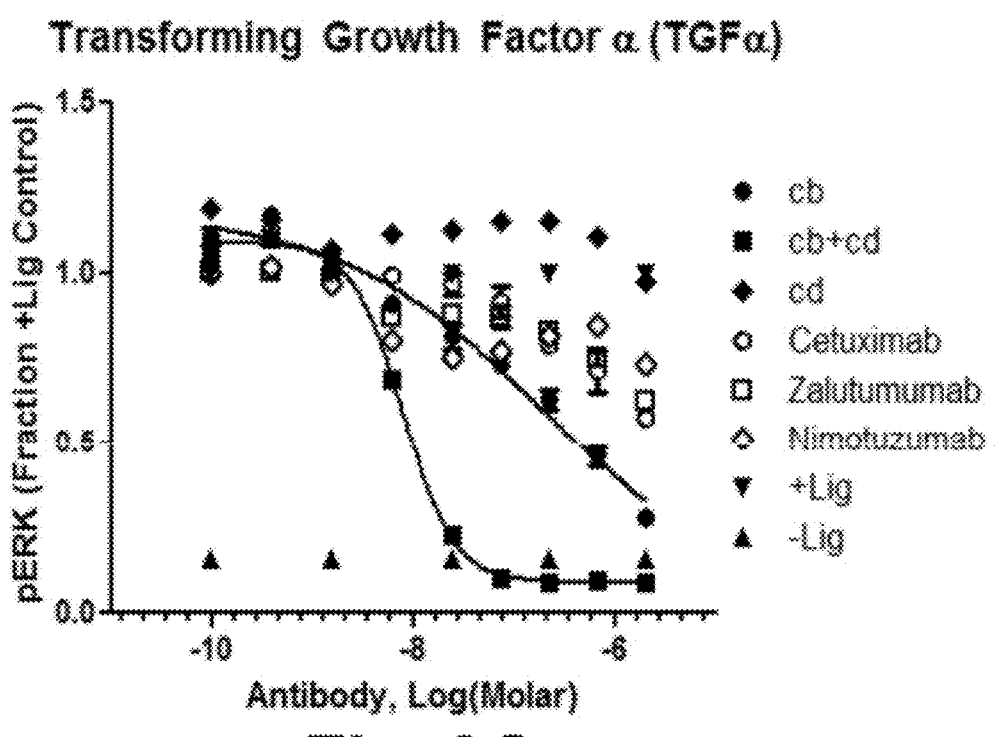
Figure 4A:
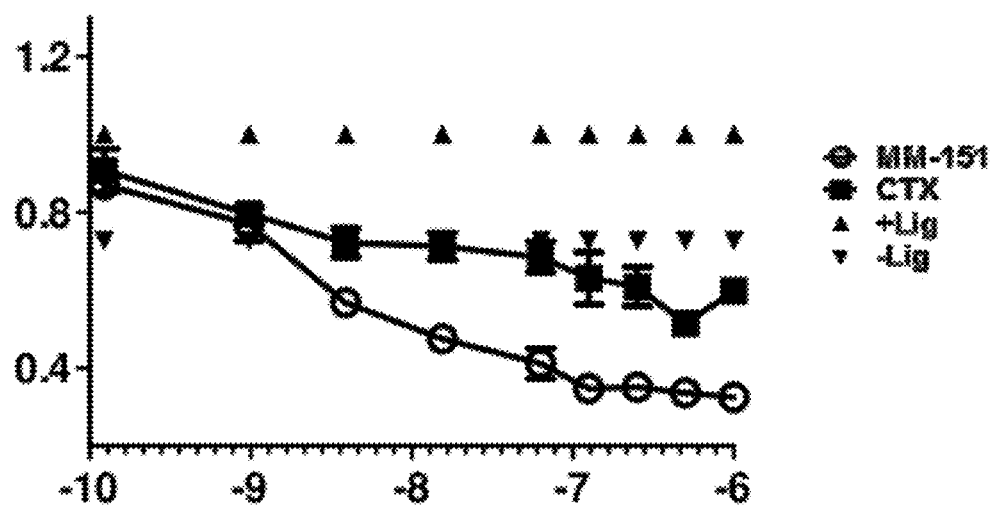
FIGS. 4A-4L: Inhibition of high affinity EGFR ligand-mediated tumor cell proliferation. H322M cells (FIGS. 4A-4D), H1975 cells (FIGS. 4E-4H), and LIM1215 cells (FIGS. 4I-4L) were treated with varying concentrations of anti-EGFR monoclonal and oligoclonal antibodies in the presence of EGFR ligands. Cells were treated with 200 ng/ml amphiregulin (AREG) (FIGS. 4A, 4E, and 4I), 50 ng/ml EGF (FIGS. 4B, 4F, and 4J), 50 ng/ml TFGα (FIGS. 4C, 4G, and 4K) or 90 ng/ml HB-EGF (FIGS. 4D, 4H, and 4L) in the presence of varying concentrations of MM-151 (open circles or cetuximab (CTX, solid squares; Bristol-Myers Squibb). Cells treated with ligand (+Lig, upward arrow) or without ligand (−Lig, downward arrow) in the absence of antibody treatment served as controls. The y-axes represent cell viability as the fraction of the viability of the amphiregulin-treated control cells and the x-axes represent antibody concentration in Log(Molar).
Figure 4B:
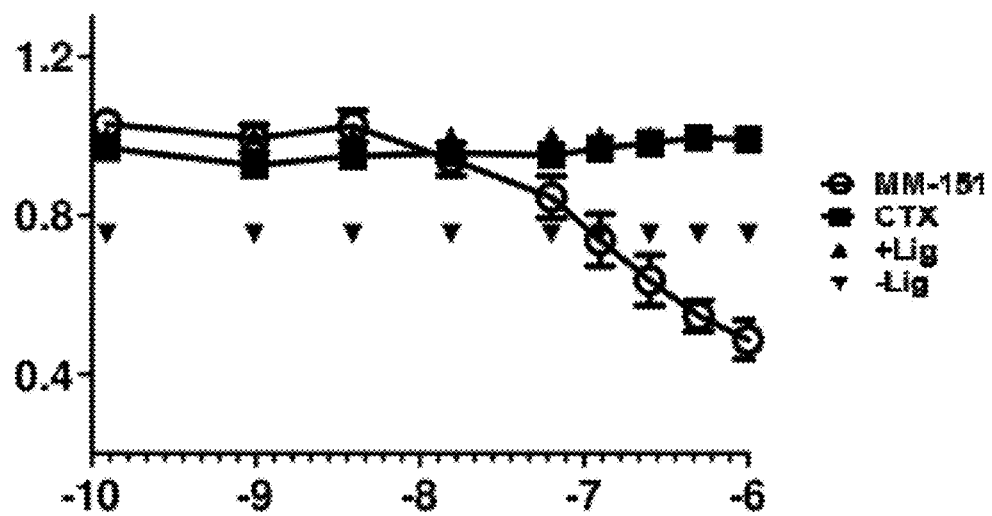
Figure 4C:
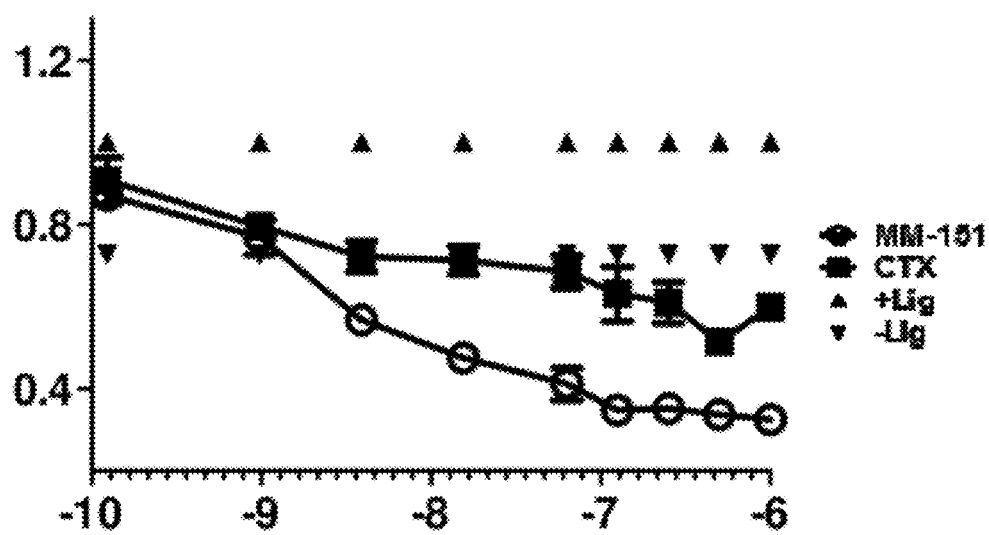
Figure 4D:
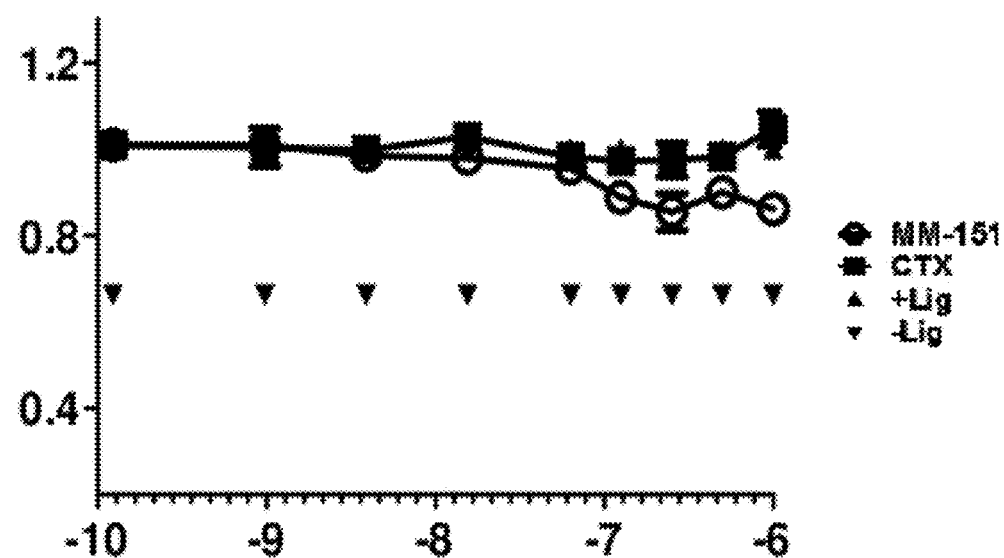
Figure 4E:
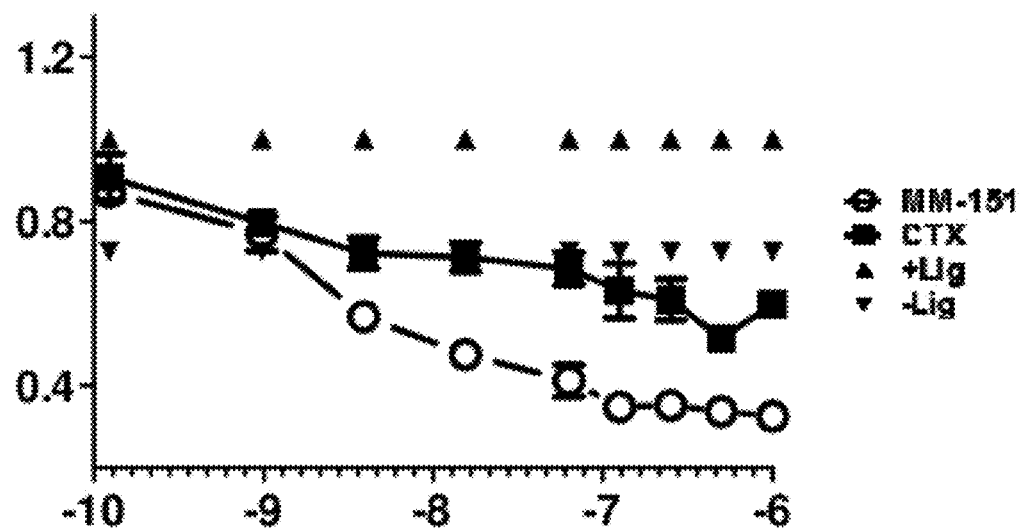
Figure 4F:
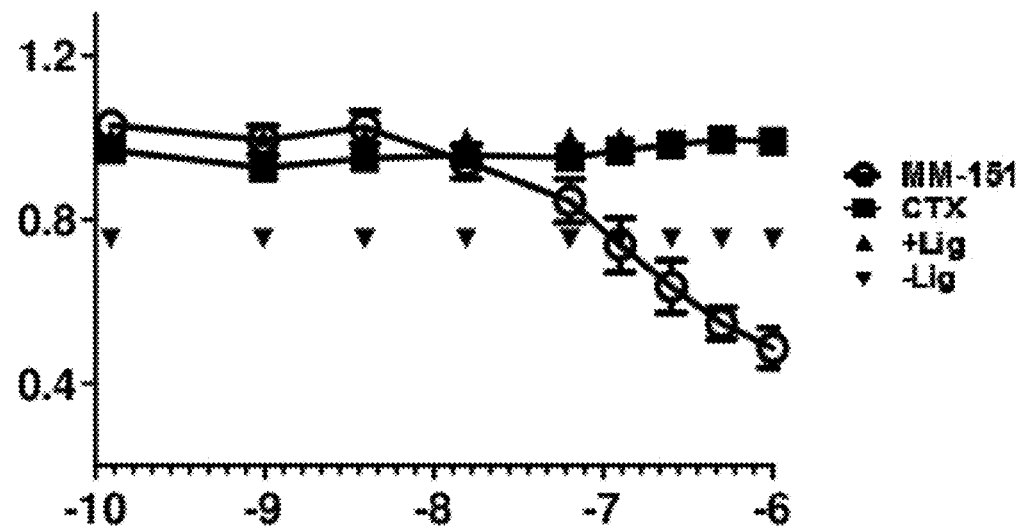
Figure 4G:
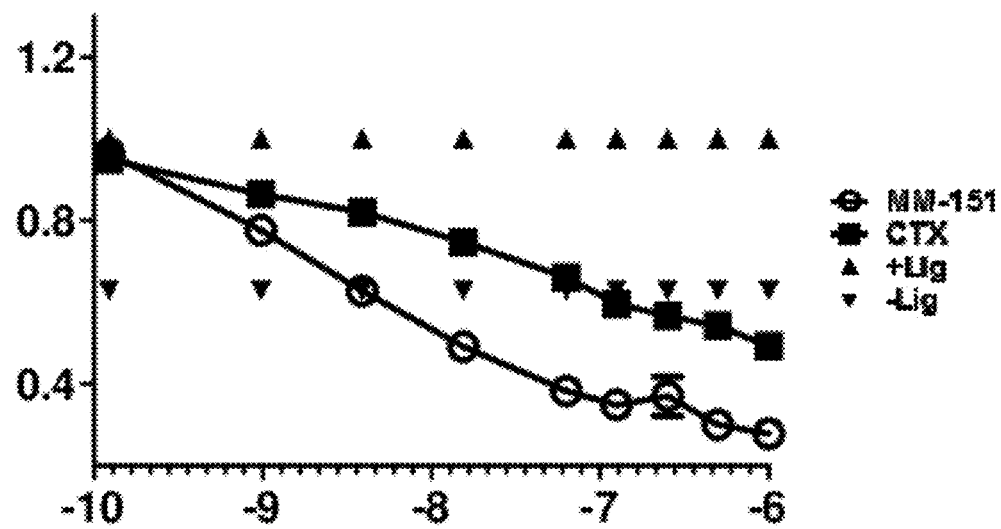
Figure 4H:
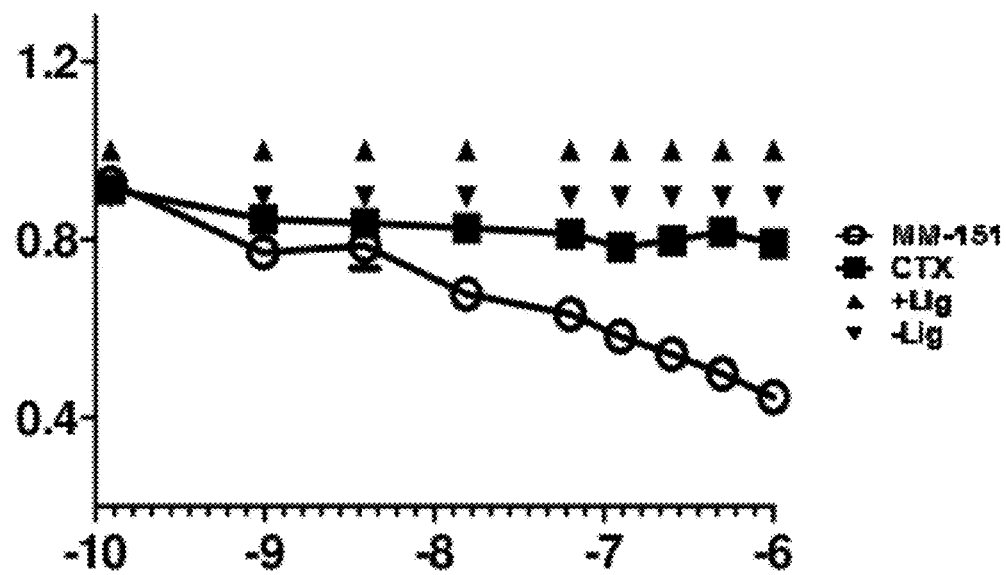
Figure 4I:
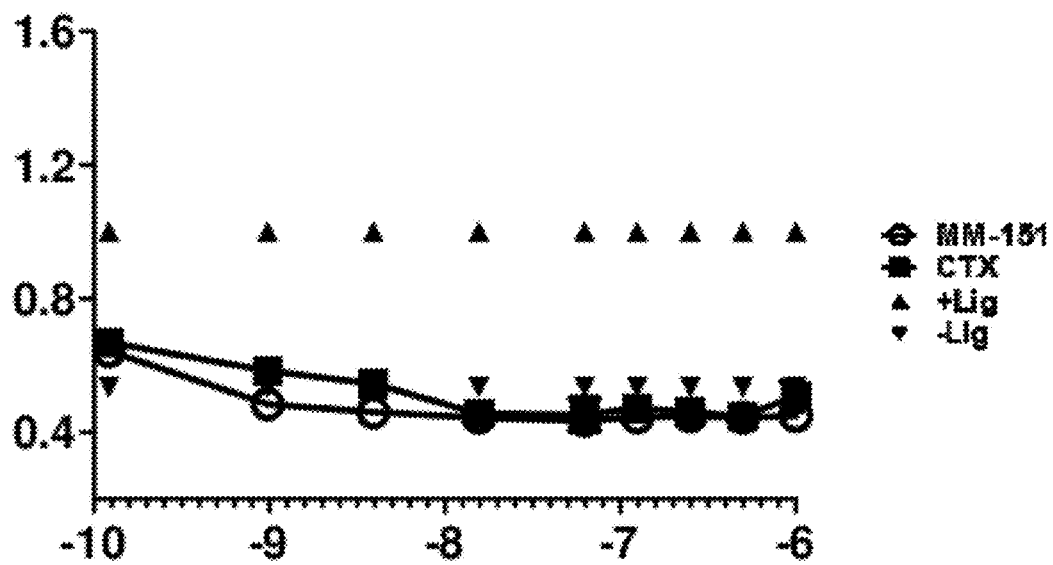
Figure 4J:
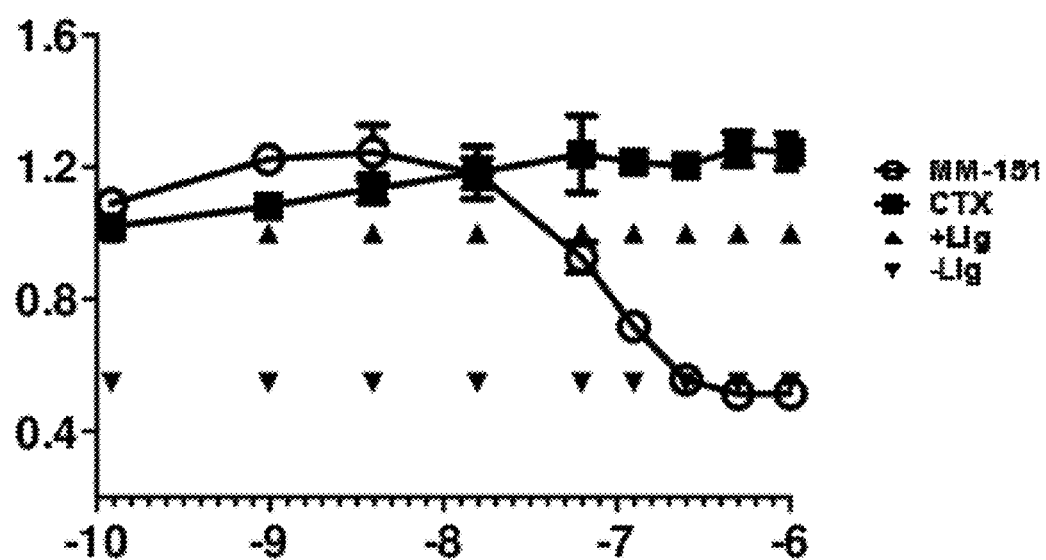
Figure 4K:
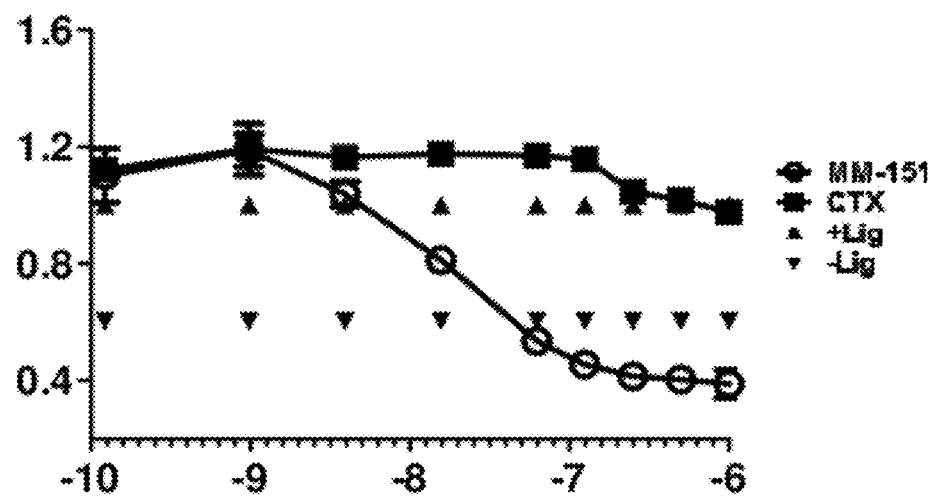
Figure 4L:
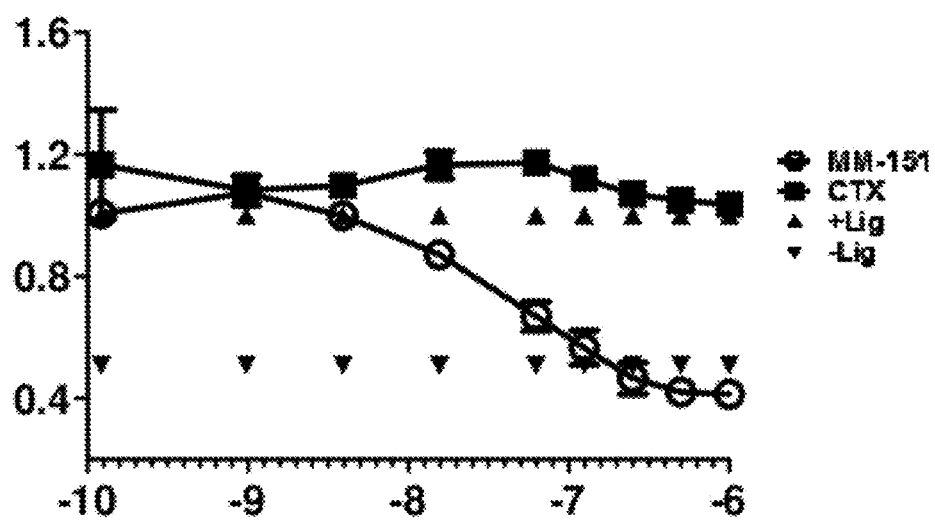
Figure 5A:
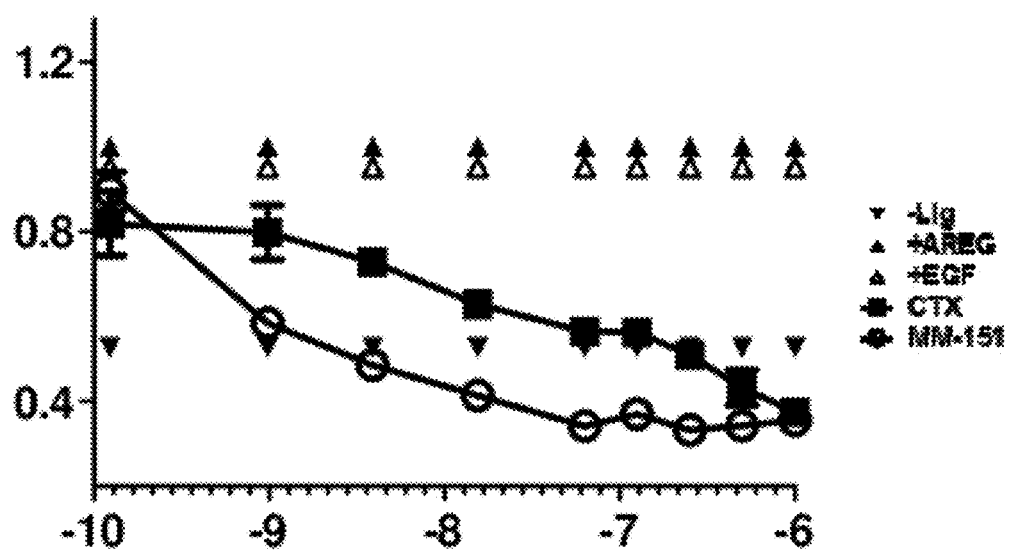
FIGS. 5A-5L: Effect of EGFR high affinity ligand titration on cell responsiveness to anti-EGFR inhibitors in vitro. The non-small cell lung cancer (NSCLC) lines H322M (FIGS. 5A-5D), HCC827 (FIGS. 5E-5H), and H1975 (FIGS. 5I-5L) were tested. Controls were growth in media with amphiregulin alone (+AREG, 200 ng/ml) or EGF alone as a control (+EGF, 20 ng/ml) or no added ligand (−Lig). Treatments were with varying concentrations (0.1-1 μM final concentration) of MM-151 or cetuximab (CTX) in the following conditions: amphiregulin alone (200 ng/ml, FIGS. 5A, 5E, and 5I); a 1000:1 amphiregulin:EGF ratio (0.2 ng/ml EGF, FIGS. 5B, 5F, and 5J); a 100:1 amphiregulin:EGF ratio (2 ng/ml EGF, FIGS. 5C, 5G, and 5K); and a 10:1 amphiregulin:EGF ratio (20 ng/ml EGF, FIGS. 5D, 5H, and 5L). The y-axes represent cell viability as a fraction of the viability of the AREG-treated control cells, whereas and the x-axes represent antibody concentration in Log(Molar).
Figure 5B:
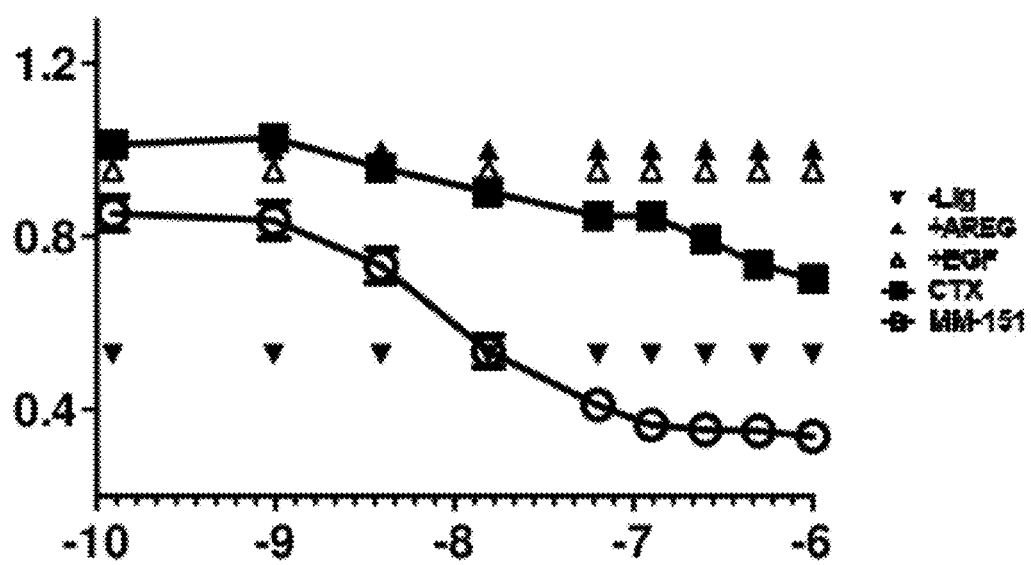
Figure 5C:
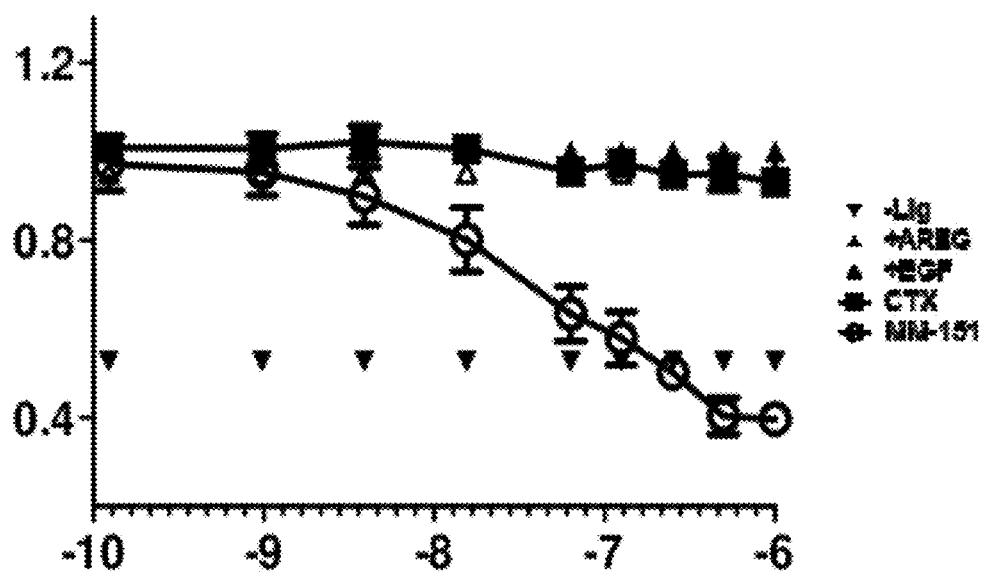
Figure 5D:
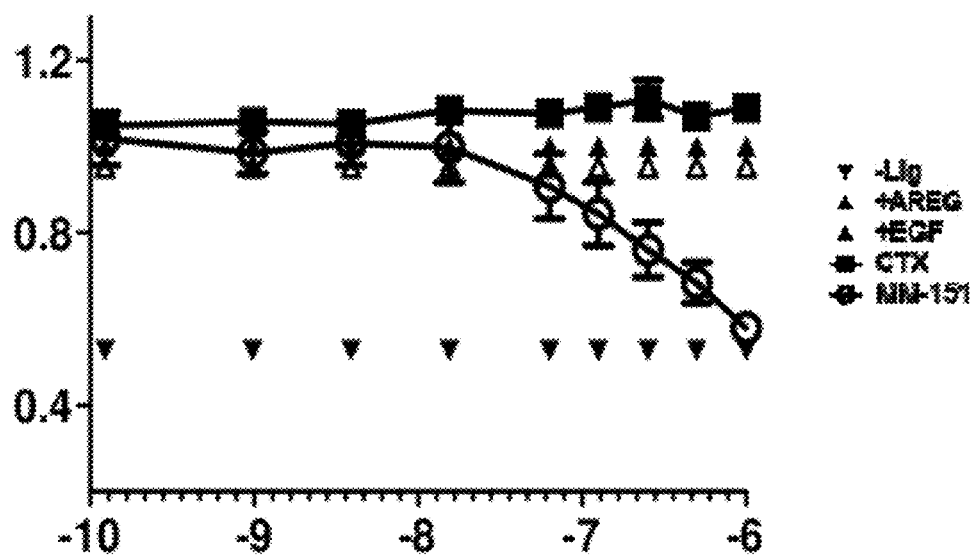
Figure 5E:
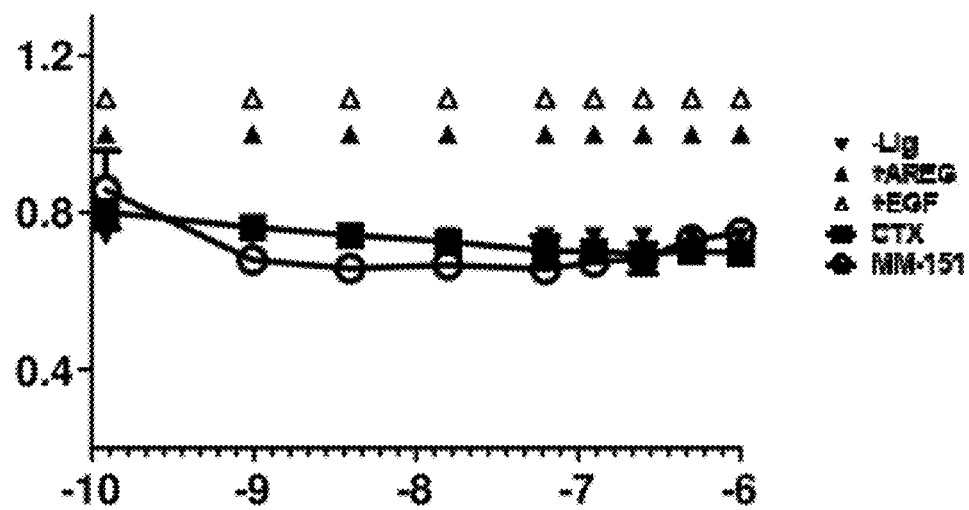
Figure 5F:
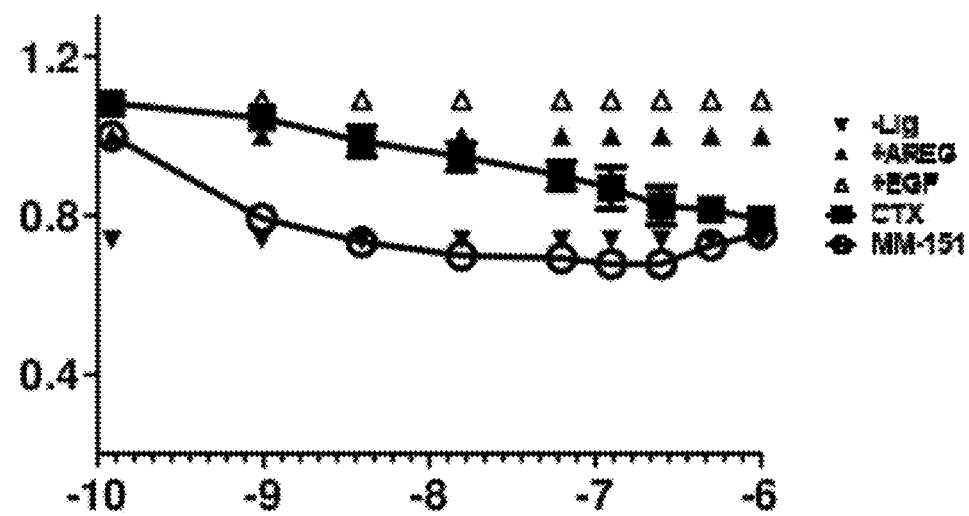
Figure 5G:
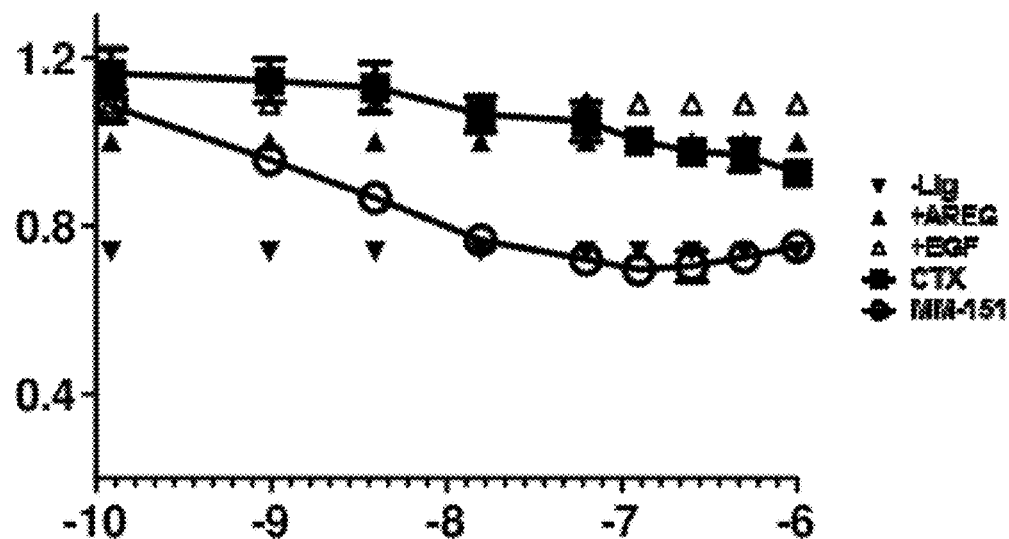
Figure 5H:
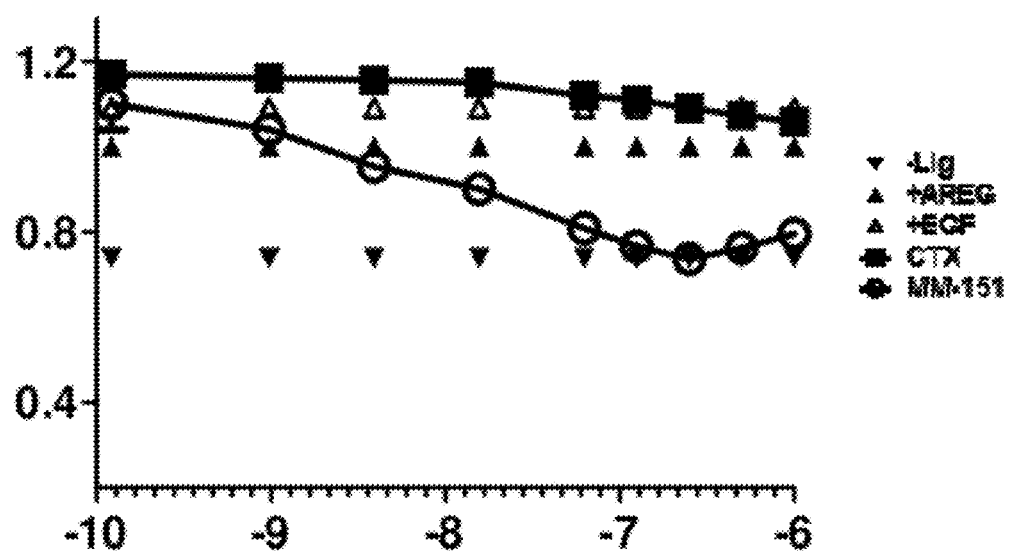
Figure 5I:
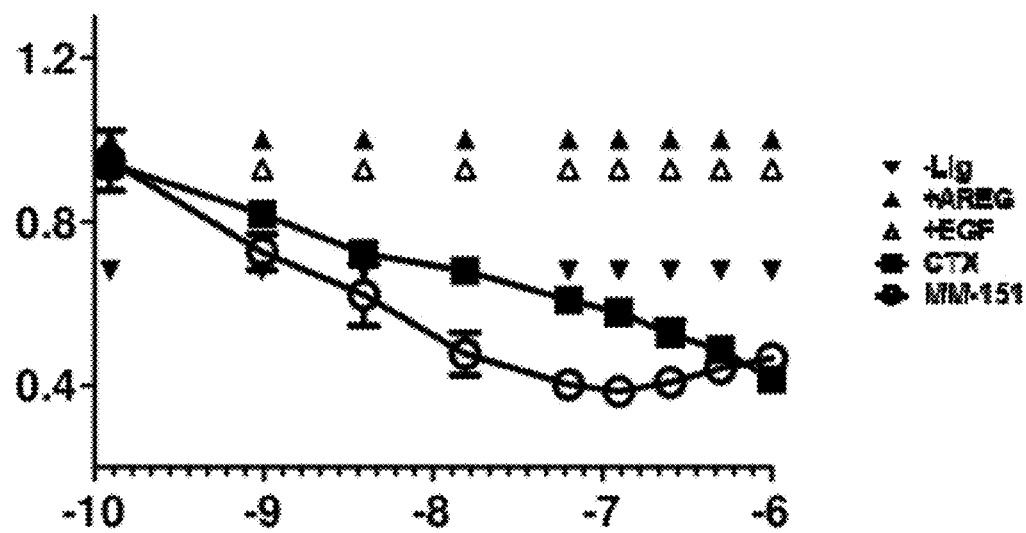
Figure 5J:
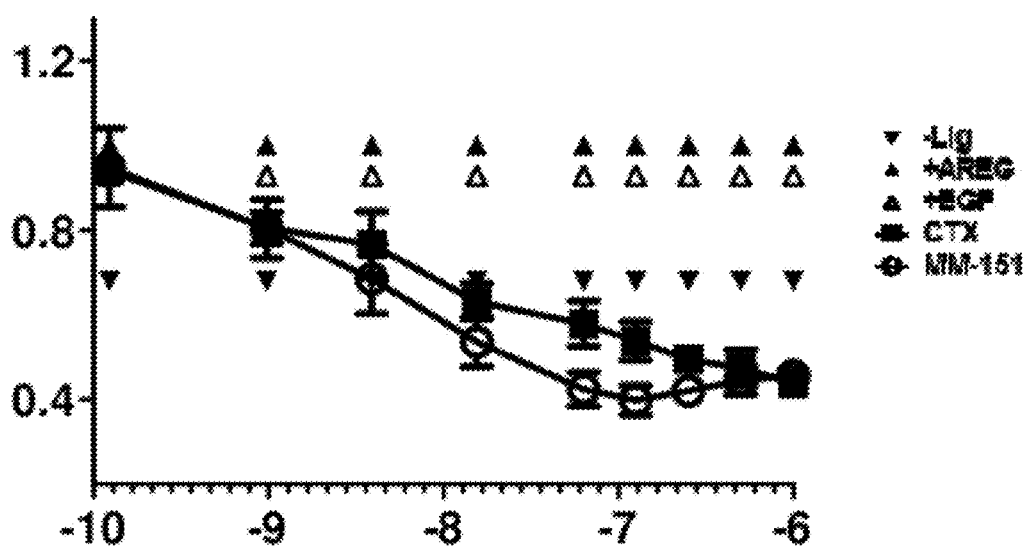
Figure 5K:
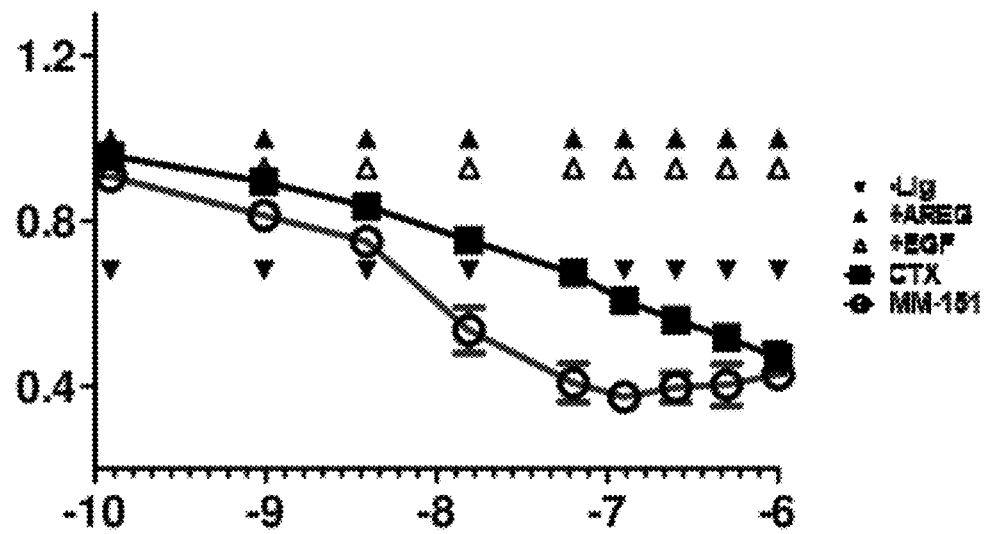
Figure 5L:
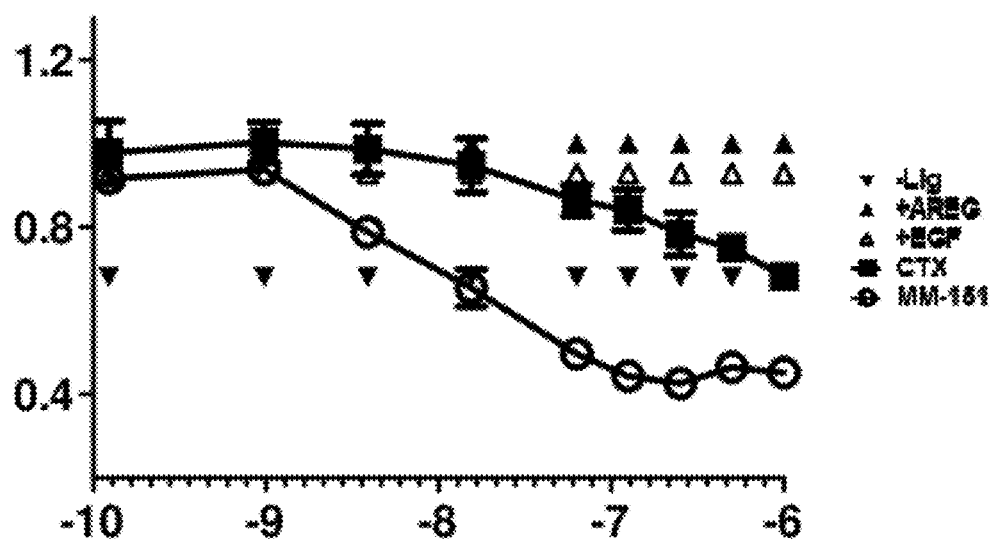

Phospho-EGF Receptor and Phospho-ERK Signaling Inhibition by Single and Pairwise Combinations of Bin 1+Bin 2 or Bin 1+Bin 3 Antibodies and Comparisons with Each of Individual Monoclonal Antibodies Cetuximab, Nimotuzumab, and Zalutumumab A431 cells were treated with single antibodies or antibody pairs and their ability to inhibit EGFR-dependent signaling was compared to that each of cetuximab, nimotuzumab, and zalutumumab. Cells were incubated with varying concentrations of anti-EGFR antibodies for 2 hrs, and then stimulated with an EGFR ligand for 10 minutes at 37° C. and 5% carbon dioxide. The seven recombinant human EGFR ligands used individually were 100 ng/ml amphiregulin ("AREG," R&D Systems, cat #262-AR/CF), 100 ng/ml betacellulin (R&D Systems, cat #261-CE-050/CF), EGF (PreproTech, cat #AF-100-15), 220 ng/ml epigen (epithelial mitogen homolog, PreproTech, cat #100-51), 150 ng/ml epiregulin (R&D Systems, cat #1195-EP/CF), 90 ng/ml HB-EGF (heparin-binding EGF-like growth factor, PreproTech, cat #100-47), and 50 ng/ml TFGα (transforming growth factor alpha, R&D Systems, cat #239-A). ELISA measurements were performed as described above for pERK and pEGFR signaling and the results are shown in FIGS. 1A-C. Only mixtures of Bin1/Bin2 antibodies cb and cd (FIG. 1A) and Bin1/Bin3 antibodies cb and ch (FIG. 1C) were effective at completely inhibiting phospho-ERK signaling when compared to cetuximab, nimotuzumab, and zalutumumab, as well as to individual components cb, cd, and ch. All antibodies, including the mixtures, were effective at complete inhibition of Phospho-EGF receptor signaling, with the exception of nimotuzumab (FIG. 1B).

Example 2

Phospho-ERK Signaling Inhibition by Single and Pairwise Combinations of Bin 1, Bin 2, and Bin 3 Antibodies and Comparisons with Cetuximab, Nimotuzumab, and Zalutumumab Single antibodies cb, cd, and ch, or pairs of cb and cd or cb and ch, (as described above in Example 1) were used to treat A431 cells at indicated total concentrations, and their ability to inhibit EGFR ligand-dependent signaling was compared to that of each single anti-EGFR antibodies cetuximab, nimotuzumab, and zalutumumab at the same concentrations. Cells were incubated with antibody for 2 hours followed by stimulation with EGFR ligand for 10 minutes. Seven EGFR ligands were used individually: amphiregulin (100 ng/ml), betacellulin (100 ng/ml), EGF (50 ng/ml), epigen (220 ng/ml), epiregulin (150 ng/ml), HB-EGF (90 ng/ml), and TFGα (50 ng/ml). Experiments were performed as described above and the results are shown in FIGS. 2A-G and 3A-G. Individually, cb and cd, as well as well cetuximab, nimotuzumab, and zalutumumab, were effective at inhibiting phospho-ERK signaling (i.e., inhibiting phosphorylation of ERK1 and ERK2) in response to the three ligands with low affinity for EGF receptor (amphiregulin, epigen, and epiregulin), but not in response to the four ligands with high affinity for EGF receptor (betacellulin, EGF, HB-EGF, and TFGα). Only oligoclonal mixtures of Bin1/Bin2 antibodies cb and cd (FIGS. 2A-G) and Bin1/Bin3 antibodies cb and ch (FIGS. 3A-G) were effective at essentially completely inhibiting phospho-ERK signaling in response to all seven (both high- and low-affinity) EGFR ligands when compared to individual components of the mixtures, cb, cd, and ch and the other tested individual monoclonal antibodies, cetuximab, nimotuzumab, and zalutumumab.

Example 3

Effect of EGFR Ligand Concentration on Phospho-ERK Cell Signaling

Figure 6:
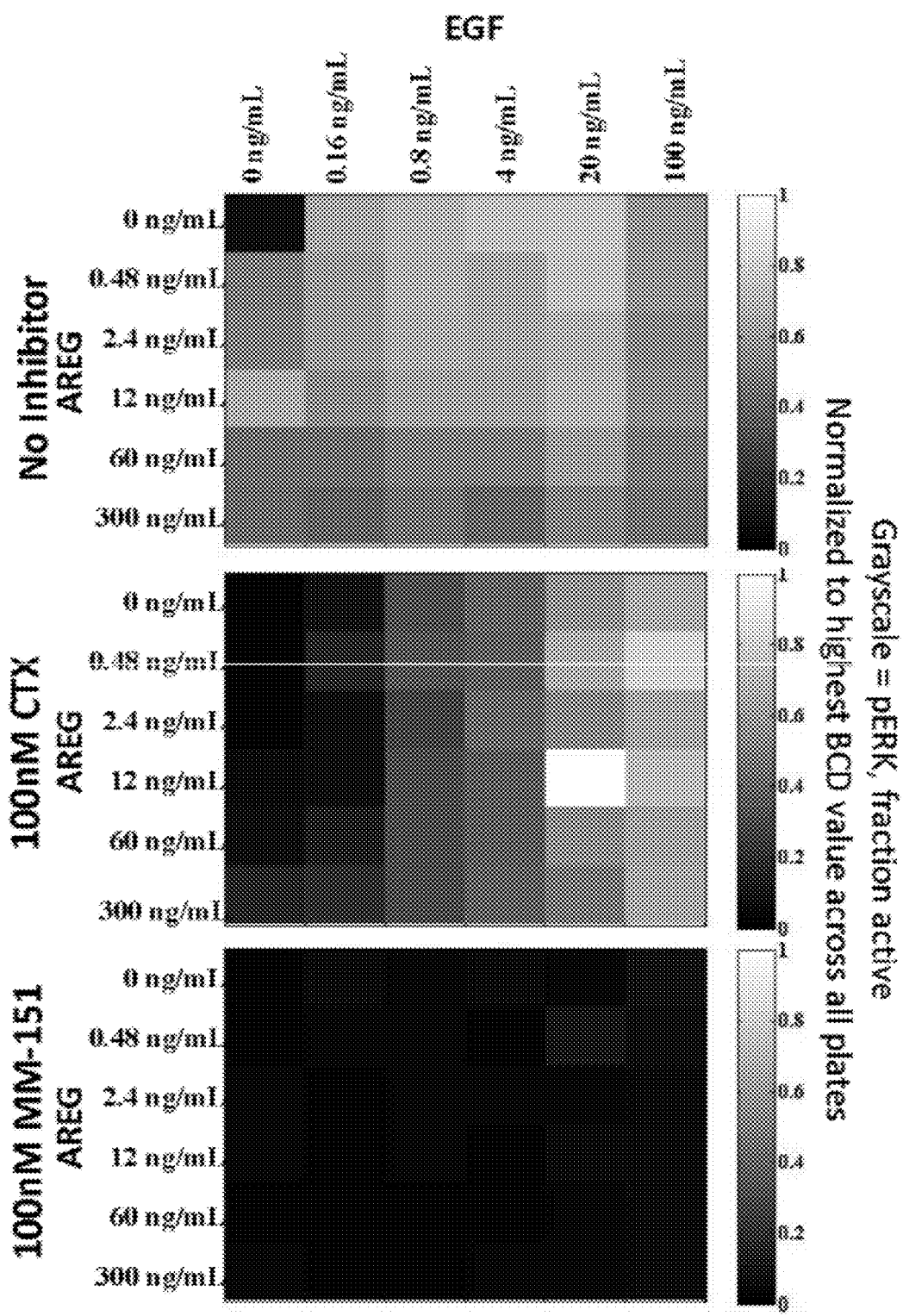
FIG. 6: Effect of EGFR ligand concentration on phopho-ERK cell signaling. The epidermoid cancer cell line A431 was treated with media alone ("No Inhibitor"), MM-151 (100 nM) or cetuximab (100 nM) for 2 hrs, followed by the addition of various concentrations of EGF (0.16 ng/ml, 0.8 ng/ml, 4.0 ng/ml, 20 ng/ml, 100 ng/ml) or AREG (0.48 ng/ml, 2.4 ng/ml, 12 ng/ml, 60 ng/ml, 300 ng/ml), alone or in combination. Cells were incubated with the various EGF and AREG ligand combinations for 10 minutes, lysed, and levels of ERK phosphorylation measured by phospho-ERK ELISA.

Inhibition of tumor cell signaling in vitro is analyzed by the methods described above or minor variations thereof. The epidermoid cancer cell line A431 was treated with media alone ("No Inhibitor"), MM-151 (100 nM) or cetuximab (100 nM) for 2 hrs, followed by the addition of various concentrations of EGF (0.16 ng/ml, 0.8 ng/ml, 4.0 ng/ml, 20 ng/ml, 100 ng/ml) or AREG (0.48 ng/ml, 2.4 ng/ml, 12 ng/ml, 60 ng/ml, 300 ng/ml), alone or in combination, as shown in FIG. 6. Cells were incubated with the various EGF and AREG ligand combinations for 10 minutes, lysed, and levels of ERK phosphorylation measured by phospho-ERK ELISA and analyzed as indicated in the methods. FIG. 6 shows MM-151 and cetuximab-mediated modulation of ERK signaling represented as fraction of the highest signal across all treatments. Phospho-ERK signaling is inhibited by cetuximab in A431 cells under low-affinity EGFR ligand (AREG) stimulation, but become increasingly resistant to inhibition upon the addition of increasing amounts of the high-affinity EGFR ligand, EGF (middle panel), while inhibition of signaling by MM-151 is largely maintained under all conditions (lower panel).

Example 4

Inhibition of Tumor Cell Proliferation in the Presence of High or Low Affinity EGFR Ligands Inhibition of Tumor Cell Proliferation In Vitro
Inhibition of cellular proliferation of cells expressing EGFR is examined in vitro as follows: H322M (NCI, Frederick, Md. 21701), H1975 (ATCC CRL-2868™), and LIM1215 (Cell Bank Australia, NSW 2145) cancer cells are separately seeded in 96 well tissue culture plates at 5,000 cells per well and grown in RPMI-1640 medium supplemented with antibiotics, 2 mM L-glutamine and 10% fetal calf serum (FCS) (H322M and H1975) or RPMI-1640 medium supplemented with 25 mM HEPES, antibiotics, 2 mM L-glutamine, 10% FCS, 0.6 µg/ml insulin, 1 µg/ml hydrocortisone and 10 µM thioglycerol (LIM1215) for 24 hours at 37 degrees Celsius and 5% carbon dioxide. Medium is then switched to RPMI-1640 with antibiotics, 2 mM L-glutamine, 1% FBS (for H322M and H1975) or RPMI-1640 with 25 mM HEPES, antibiotics, 2 mM L-glutamine, 1% FCS, 0.6 µg/ml Insulin, 1 µg/ml hydrocortisone and 10 µM thioglycerol (for LIM1215) supplemented with 200 ng/ml AREG, 50 ng/ml EGF, 50 ng/ml TGFα or 90 ng/ml HB-EGF in the presence of varying concentrations of MM-151 or cetuximab (Bristol-Myers Squibb). Cell viability is measured 72 hours post-treatment using the CellTiter-Glo® (CTG) Luminescent Viable Cell Number Assay (Promega Corporation) according to manufacturer's instructions. The CTG assay measures the number of viable cells in culture based upon quantitation of ATP present, which is an indicator of metabolically active cells. Control treatments include cells treated with 1% FCS-containing medium (as detailed above) in the presence ("+Lig") or absence ("−Lig") of the respective ligand treatment. Viable cell numbers are plotted in GraphPad Prism (GraphPad Software, La Jolla, Calif.) as a fraction of the respective ligand ("+Lig") treatment control.

Results
The non-small cell lung cancer (NSCLC) lines H322M and H1975 and colon cancer cell line LIM1215 were treated with varying concentrations of MM-151 or cetuximab (0.1-1 µM final concentration). Potent inhibition of growth of H322M, H1975 and LIM1215 cells was obtained over a range of MM-151 concentrations in the presence of high affinity EGFR ligands (EGF, TGFα, HB-EGF), but not in the presence of cetuximab or in assay medium alone (1% FCS)—FIGS. 4 (B-D, F-H, and J-L). Potent inhibition of growth of H322M, H1975 and LIM1215 cells was obtained over a range of concentrations for both MM-151 and cetuximab, but not by assay medium alone (1% FCS) in the presence of the low affinity EGFR ligand amphiregulin (AREG)—FIGS. 4 (A, E and I). These data demonstrate the ability of the MM-151 oligoclonal mixture to inhibit tumor cell proliferation in vitro in response to both high-affinity (EGF, TGFα, HB-EGF) and low-affinity (AREG) ligands, whereas cetuximab is only potently effective in cells treated with low-affinity (AREG) ligand.

Example 5

Effects of EGF Ligand Concentration On Cell Proliferation

Using methods essentially as described in the preceding Example, non-small cell lung cancer (NSCLC) cell lines H322M, HCC827 and H1975 were treated with AREG alone (200 ng/ml) or with AREG plus increasing amounts of EGF (0.2, 2, 20 ng/ml) in the presence of varying concentrations of MM-151 or cetuximab (0.1-1 µM final concentration).
Results
The NSCLC cell lines respond to cetuximab under low-affinity EGFR ligand stimulation (AREG), but become increasingly unresponsive to treatment upon the addition of increasing amounts of the high-affinity EGFR ligand EGF, while sensitivity to MM-151 is largely maintained (see FIGS. 5A-5L).

Example 6

Assays and Kits

Measurement of EGFR Family Ligand Expression Levels by RT-qPCR
Measurement of EGFR ligand expression in tumor biopsy samples by real-time quantitative polymerase chain reaction (RT-qPCR) of DNAs reverse transcribed from RNAs is carried out as follows:
Total RNA is isolated from patient biopsy/tumor samples, e.g., by commercially available standard methods. The method of total RNA isolation may be any method (including conventional methods) suitable for use with the type of patient biopsy sample being tested, e.g., fresh, fixed, frozen, formalin fixed paraffin embedded (FFPE), etc. Total RNA is then converted to cDNA using the gene specific primers described below and Qiagen® OneStep RT-PCR reagents and protocol (Cat. #210210, Qiagen, Germantown, Md.). The cDNA is then used for RT-qPCR using the following gene specific primers as TaqMan® probe sets obtained from Applied Biosystems (Carlsbad, Calif.) along with reagents and equipment from the same source, all as described below:

1. TaqMan® Gene Expression Assay, Gene Name: beta-cellulin, Assay ID: Hs01101201_ml
2. TaqMan® Gene Expression Assay, Gene Name: transforming growth factor, alpha, Assay ID: Hs00608187_ml
3. TaqMan® Gene Expression Assay, Gene Name: heparin-binding EGF-like growth factor, Assay ID: Hs00181813_ml
4. TaqMan® Gene Expression Assay, Gene Name: epiregulin, Assay ID: Hs00914313_ml
5. TaqMan® Gene Expression Assay, Gene Name: amphiregulin, Assay ID: Hs00950669_ml
6. TaqMan® Gene Expression Assay, Gene Name: epidermal growth factor, Assay ID: Hs01099999_ml.
7. TaqMan® Gene Expression Assay, Gene Name: epithelial mitogen homolog (epigen), Assay ID Hs02385425_ml.

5 µl of diluted cDNA is mixed with 10 µl of TaqMan® Fast Advanced Master Mix (Cat. # 4444556), 2 µl of the above primer probe set and 3 µl of water in a MicroAmp® Fast Optical 96-Well Reaction Plate (Cat. #4366932). The plate is then placed in a Viia™ 7 RT-qPCR machine and a thermal cycling program completed as described in the manufacturers protocol. Data collection and analysis is carried out using the Viia™ 7-RUO-Software (Applied Biosystems).

Also see US Patent Publication Nos. 20030165952, 20040009489, 20050095634, 20050266420, 20070141587, 20070141588, 20070141589, 20080182255, 20090125247, 20090280490, 20100221754 and 20110086349, and U.S. Pat. Nos. 6,750,013, 6,808,888, 6,939,670, 6,964,850, 6,692,916, 7,081,340, 7,171,311, 7,526,387, 7,569,345, 7,622,251, 7,871,769, 7,838,224, 7,858,304, 7,930,104, and 8,071,286.

Equivalents

Those skilled in the art will recognize, or be able to ascertain using no more than routine experimentation, many equivalents of the specific embodiments described herein. Such equivalents are intended to be encompassed by the following claims. Any combination of the embodiments disclosed in the any plurality of the dependent claims is contemplated to be within the scope of the disclosure.

What is claimed is:

1. A method for determining whether a patient having a tumor is predicted to have an unfavorable outcome as a result of treatment #1 with a monoclonal anti-EGFR antibody preparation comprising a single species of monoclonal antibody, and a favorable outcome as a result of treatment #2 with an oligoclonal anti-EGFR antibody preparation comprising a plurality of species of monoclonal anti-EGFR antibodies, one against each of at least two extracellular epitopes of EGFR, or, whether the patient is predicted to have the favorable outcome as a result of treatment #2 and as a result of treatment #1;

the method comprising:

obtaining a biopsy sample of the tumor and:

a) measuring levels of protein of, or of RNAs coding for, at least two low affinity EGFR ligands selected from amphiregulin, epigen, or epiregulin in the biopsy sample, b) measuring levels of protein of, or of RNAs coding for, at least two high affinity EGFR ligands selected from betacellulin, EGF, HB-EGF or TGFα in the biopsy sample, wherein all of the levels measured in a) and b) are protein levels or all of the levels measured in a) and b) are RNA levels, and c) comparing the average level of protein of, or of RNAs coding for, each of the high affinity EGFR ligands measured in a) to the average level of protein of, or of RNAs coding for, each of the low affinity EGFR ligands measured in b);

and wherein, if the average level of protein of, or of RNAs coding for, low affinity EGFR ligands measured in a) is greater than the average level of protein of, or of RNAs coding for, high affinity EGFR ligands measured in b), the patient is predicted to have the favorable outcome as a result of treatment #1 and the patient is also predicted to have the favorable outcome as a result of treatment #2, and if the average level of protein of, or of RNAs coding for, low affinity EGFR ligands measured in a) is less than or equal to the average level of protein of, or of RNAs coding for, high affinity EGFR ligands measured in b), the patient is predicted to have an unfavorable outcome from treatment #1 and is predicted to have a favorable outcome from treatment #2.

2. The method of claim 1, wherein:

the at least two low affinity EGFR ligands is low affinity ligands.

3. The method of claim 1, wherein the at least two high affinity EGFR ligands is at least three high affinity ligands.

4. The method of claim 1, wherein the favorable outcome comprises reduction of growth of the tumor.

5. The method of claim 1, wherein the tumor is malignant.

6. The method of claim 1, wherein the method comprises measuring levels of mRNA.

7. The method of claim 1, wherein the monoclonal anti-EGFR antibody preparation comprises cetuximab, zalutumumab, matuzumab, or nimotuzumab.

8. The method of claim 1, wherein members of the plurality of anti-EGFR antibody species separately and uniquely bind to more than two different extracellular epitopes of EGFR.

9. The method of claim 8, wherein the members of the plurality of anti-EGFR antibody species separately and uniquely bind to no more than three extracellular epitopes of EGFR.

10. The method of claim 8, wherein the oligoclonal anti-EGFR antibody preparation comprises no more than three different species of monoclonal anti-EGFR antibodies.

11. The method of claim 10, wherein the oligoclonal anti-EGFR antibody preparation comprises a first monoclonal antibody comprising heavy and light chain variable regions comprising SEQ ID NOs: 1 and 2, respectively, a second monoclonal antibody comprising heavy and light chain variable regions comprising SEQ ID NOs:3 and 4, respectively, and a third monoclonal antibody comprising heavy and light chain variable regions comprising SEQ ID NOs:5 and 6, respectively.

12. The method of claim 1, wherein the tumor is a tumor of the skin, central nervous system, head, neck, esophagus, stomach, colon, rectum, anus, liver, pancreas, bile duct, gallbladder, lung, breast, ovary, uterus, cervix, vagina, testis, germ cells, prostate, kidney, ureter, urinary bladder, adrenal, pituitary, thyroid, bone, muscle or connective tissue.

13. A method of treating a patient having a tumor, the method comprising: determining, according to the method of claim 1
that the patient is predicted to have the favorable outcome as a result of treatment #2 and as a result of treatment #1, wherein the patient is treated with treatment #1.

14. The method of claim 13, wherein the tumor is a malignant tumor.

15. A method of treating a patient having a tumor, the method comprising: determining, according to the method of claim 1 that the patient is predicted to have the unfavorable outcome as a result of treatment #1 and the favorable outcome as a result of treatment #2, wherein the patient is treated with treatment #2.

16. The method of claim 1, wherein the oligoclonal anti-EGFR antibody preparation comprises one or more of cetuximab, zalutumumab, nimotuzumab and panitumumab.

17. A method for determining whether or not a monoclonal anti-EGFR antibody preparation comprising only a single species of anti-EGFR antibody should be used to treat a malignant tumor, the method comprisingobtaining a biopsy sample of the tumor and:
    a) measuring levels of protein of, or of RNAs coding for, at least two low affinity EGFR ligands selected from amphiregulin, epigen, or epiregulin in the biopsy sample,
    b) measuring levels of protein of, or of RNAs coding for, at least two high affinity EGFR ligands selected from betacellulin, EGF, HB-EGF or TGFα in the biopsy sample,
    wherein, all of the levels measured in a) and b) are protein levels or all of the levels measured in a) and b) are RNA levels, and
    c) comparing the average level of protein of, or of RNAs coding for, each of the low affinity EGFR ligands measured in a) to the average level of protein of, or of RNAs coding for, each of the high affinity EGFR ligands measured in b);
wherein,
if the average level of protein of, or of RNAs coding for, low affinity EGFR ligands measured in a) is greater than the average level of protein of, or of RNAs coding for, high affinity EGFR ligands measured in b), the monoclonal anti-EGFR antibody preparation should be used to treat the tumor, and
if the average level of protein of, or of RNAs coding for, low affinity EGFR ligands measured in a) is less than or equal to the average level of protein of, or of RNAs coding for, high affinity EGFR ligands measured in b), the monoclonal anti-EGFR antibody preparation should not be used to treat the tumor.

\* \* \* \* \*

UNITED STATES PATENT AND TRADEMARK OFFICE
CERTIFICATE OF CORRECTION

PATENT NO. : 8,691,231 B2
APPLICATION NO. : 13/488270
DATED : April 8, 2014
INVENTOR(S) : Raghida Bukhalid et al.

It is certified that error appears in the above-identified patent and that said Letters Patent is hereby corrected as shown below:

In the Claims:

At column 24, claim number 2, line numbers 52-54, please replace claim 2, which reads:

"The method of claim 1, wherein:
the at least two low affinity EGFR ligands is low affinity ligands."

with the following:

--The method of claim 1, wherein the at least two low affinity EGFR ligands is three low affinity ligands.--.

At column 26, claim number 17, line number 7, please change "malignant tumor, the method comprisingobtaining a biopsy" to --malignant tumor, the method comprising obtaining a biopsy--.

Signed and Sealed this
Fourteenth Day of October, 2014

Michelle K. Lee
*Deputy Director of the United States Patent and Trademark Office*